(12) United States Patent
Honjo et al.

(10) Patent No.: US 11,730,444 B2
(45) Date of Patent: Aug. 22, 2023

(54) IMAGE PROCESSING APPARATUS AND ULTRASOUND DIAGNOSIS APPARATUS

(71) Applicant: Canon Medical Systems Corporation, Otawara (JP)

(72) Inventors: Yasunori Honjo, Kawasaki (JP); Masaki Watanabe, Kawasaki (JP); Tetsuya Kawagishi, Nasushiobara (JP); Koichiro Kurita, Nasushiobara (JP)

(73) Assignee: Canon Medical Systems Corporation, Otawara (JP)

( * ) Notice: Subject to any disclaimer, the term of this patent is extended or adjusted under 35 U.S.C. 154(b) by 477 days.

(21) Appl. No.: 15/989,865

(22) Filed: May 25, 2018

(65) Prior Publication Data
US 2019/0000414 A1 Jan. 3, 2019

(30) Foreign Application Priority Data

Jun. 30, 2017 (JP) .................................. 2017-129714
May 8, 2018 (JP) .................................. 2018-089822

(51) Int. Cl.
*A61B 8/08* (2006.01)
*A61B 8/00* (2006.01)

(52) U.S. Cl.
CPC .............. *A61B 8/085* (2013.01); *A61B 8/488* (2013.01); *A61B 8/5207* (2013.01); *A61B 8/5269* (2013.01); *A61B 8/466* (2013.01); *A61B 8/5238* (2013.01)

(58) Field of Classification Search
CPC ....... A61B 8/085; A61B 8/488; A61B 8/5207; A61B 8/00; A61B 8/08; A61B 8/0891; A61B 8/52; A61B 8/5269; A61B 8/466; A61B 8/5238
See application file for complete search history.

(56) References Cited

U.S. PATENT DOCUMENTS

| | | | | |
|---|---|---|---|---|
| 2002/0120195 A1* | 8/2002 | Hossack | ............... | G01S 7/5205 600/443 |
| 2012/0085174 A1* | 4/2012 | Urbano | ............... | G01S 7/52079 73/602 |
| 2014/0066767 A1* | 3/2014 | Mammone | ........... | A61B 8/5269 600/442 |

FOREIGN PATENT DOCUMENTS

JP 2006087744 A * 4/2006
JP 4744833 8/2011

OTHER PUBLICATIONS

Ta et al., Automating tumor classification with pixel-by-pixel contrast-enhanced ultrasound perfusion kinetics; published online on Mar. 22, 2012; Journal of Vacuum Science & Technology B 30, 02C103 (2012); pp. 02C13-1 to 02C103-10 (Year: 2012).*

* cited by examiner

*Primary Examiner* — Chao Sheng
(74) *Attorney, Agent, or Firm* — Oblon, McClelland, Maier & Neustadt, L.L.P.

(57) ABSTRACT

An image processing apparatus according to an embodiment includes processing circuitry. The processing circuitry is configured to perform a speckle noise reducing process on each of a plurality of images that were acquired by using an ultrasound wave and are in a time series. The processing circuitry is configured to calculate an index value indicating fluttering of image signal intensities in each of multiple positions within a region of interest, on the basis of the plurality of images resulting from the speckle noise reducing process.

16 Claims, 12 Drawing Sheets

FIG.5
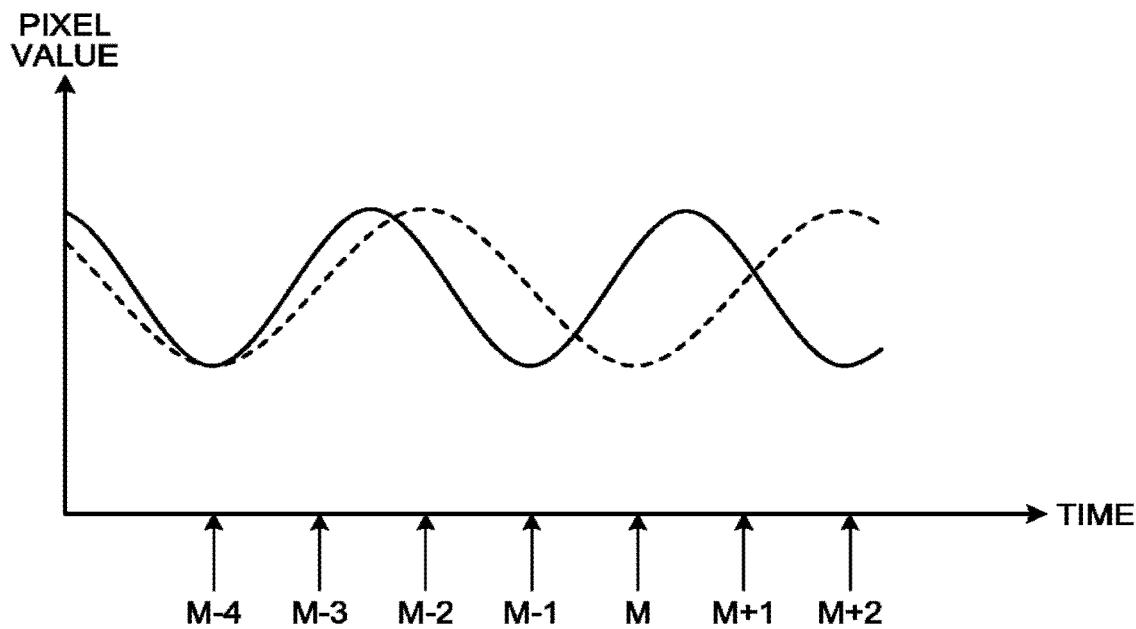
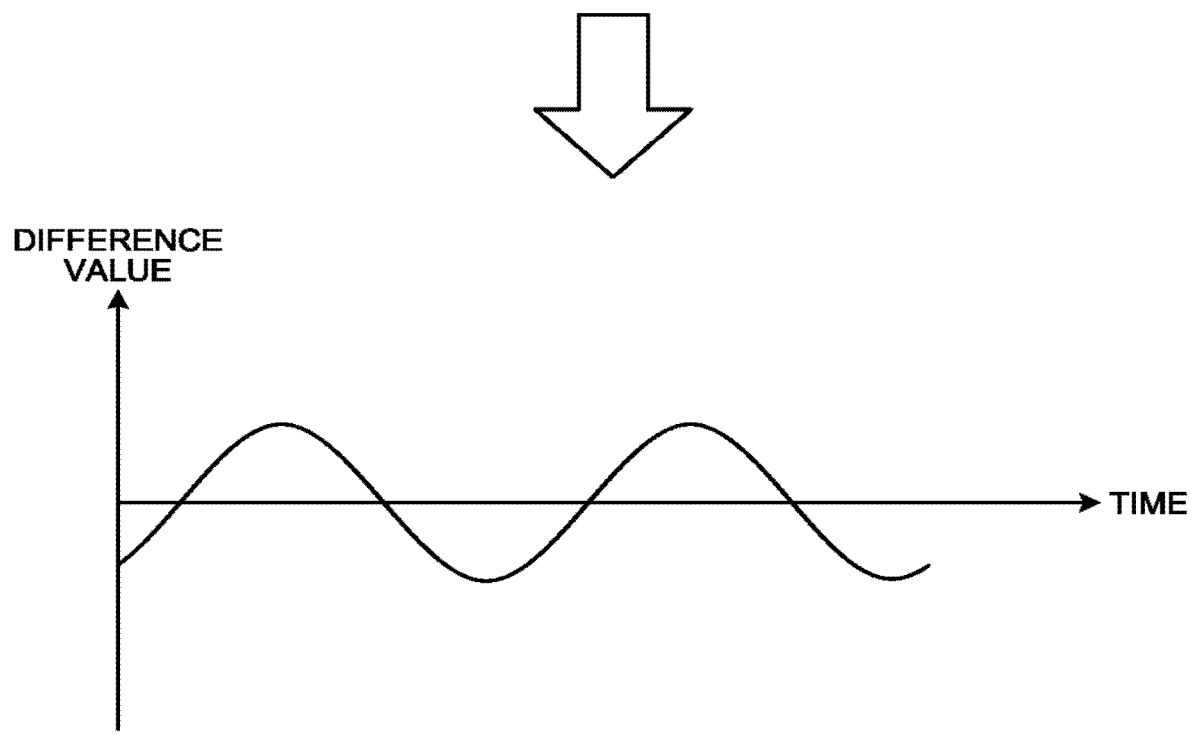

PARAMETRIC IMAGE

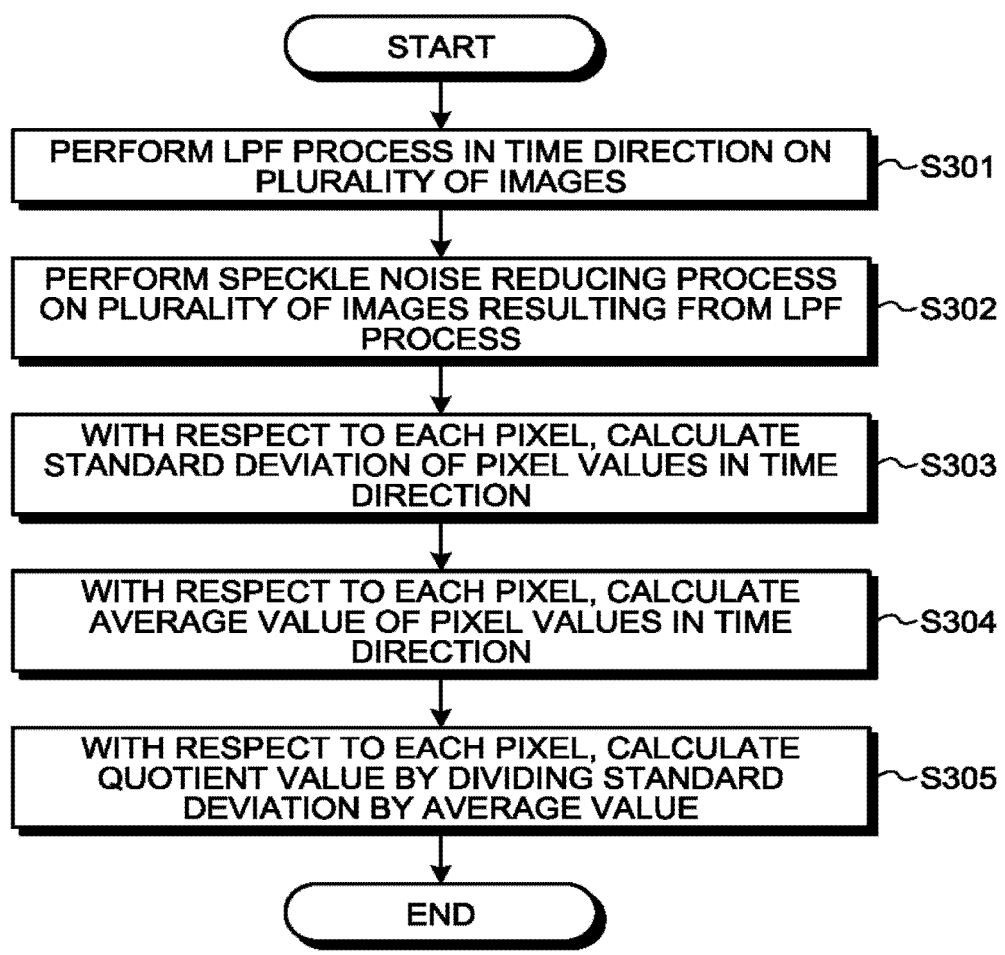

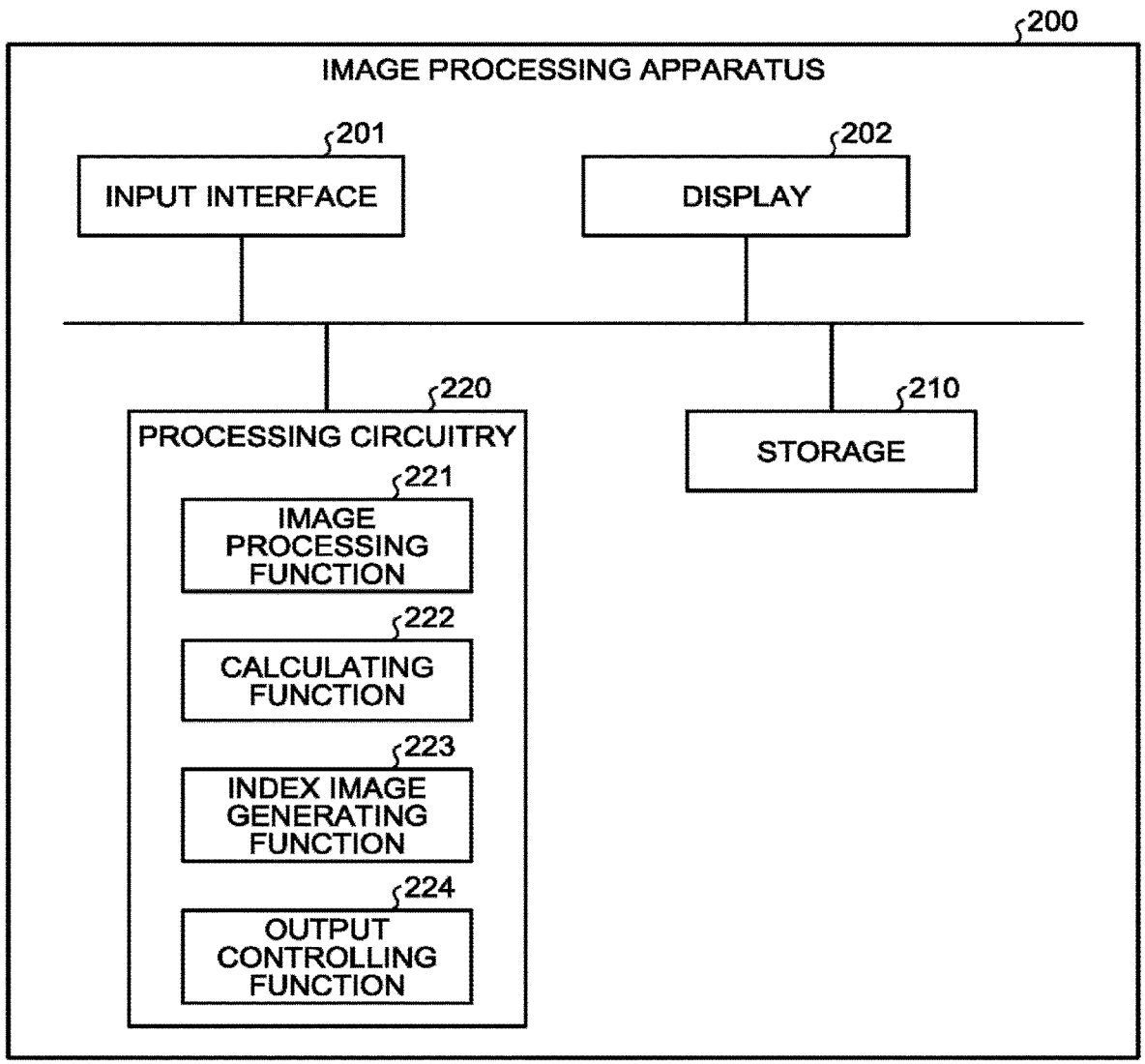
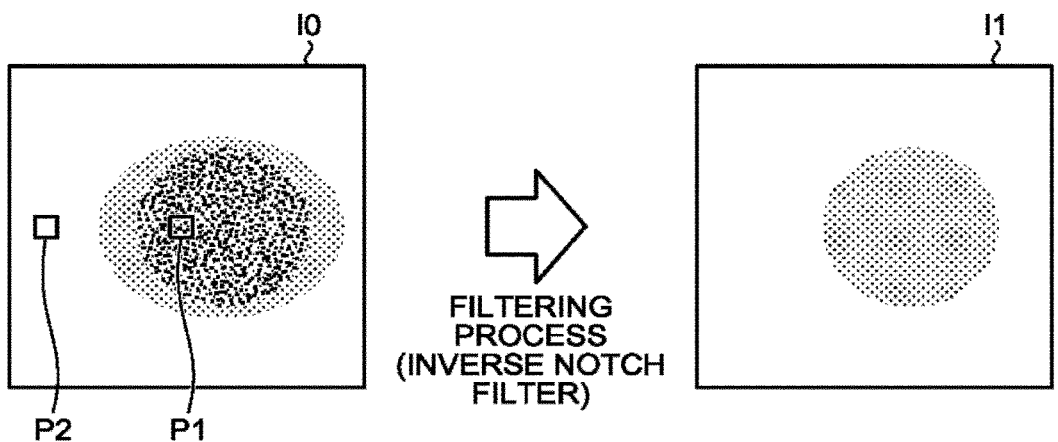

FIG.13
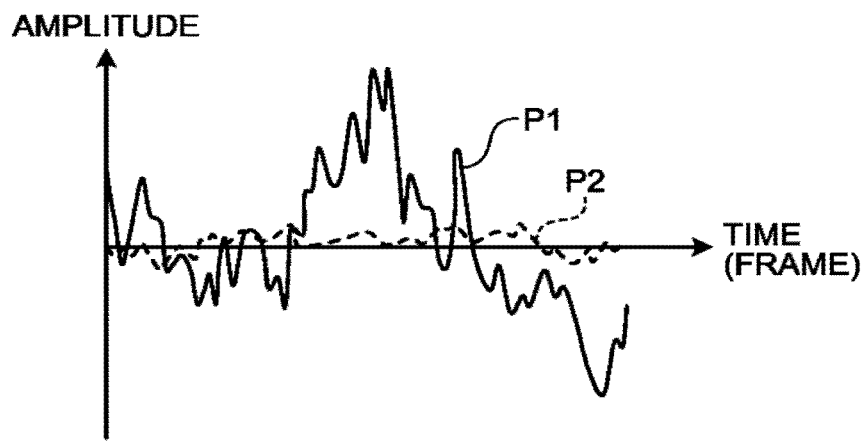
↓ FOURIER TRANSFORM
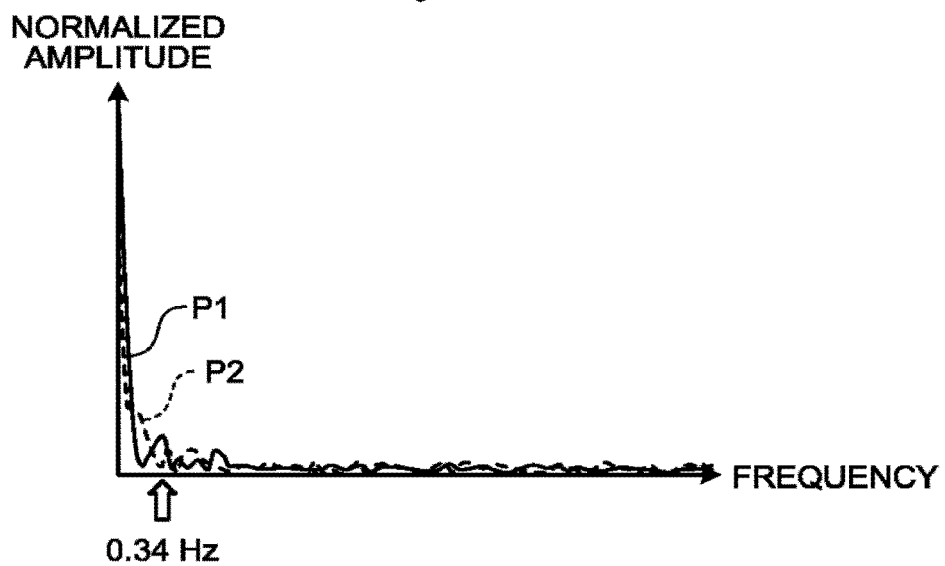
↓ PERFORM INVERSE FOURIER TRANSFORM AFTER ARRANGING FREQUENCIES OTHER THAN 0.34 Hz TO BE 0
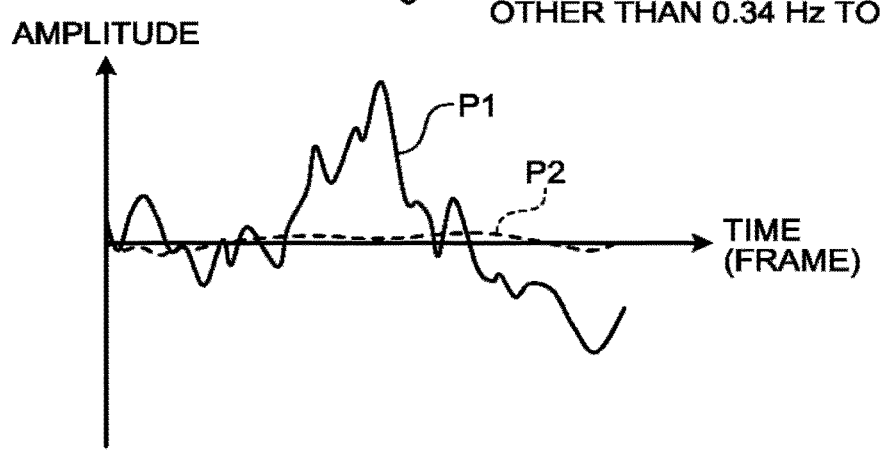

CONVERTING PROCESS

IMAGE PROCESSING APPARATUS AND ULTRASOUND DIAGNOSIS APPARATUS

CROSS-REFERENCE TO RELATED APPLICATIONS

This application is based upon and claims the benefit of priority from Japanese Patent Application No. 2017-129714, filed on Jun. 30, 2017; and Japanese Patent Application No. 2018-89822, filed on May 8, 2018, the entire contents of all of which are incorporated herein by reference.

FIELD

Embodiments described herein relate generally to an image processing apparatus and an ultrasound diagnosis apparatus.

BACKGROUND

Conventionally, judgment of whether a tumor is malignant or benign is made by performing biopsy with a tissue collected by a needle puncture or by performing an image diagnosis process to evaluate the uptake amount of a contrast agent. Because the needle puncture and administration of the contrast agent both take trouble, there is a demand for developing a method for making the judgment in an easy and convenient manner without involving those manipulations.

For example, it is reported that at least 5% of the total population have a hemangioma, which is one type of benign tumor. Accordingly, if it were possible to easily and conveniently determine whether a site suspected to have a tumor has a hemangioma or not, it would be helpful for discriminating hemangiomas from other types of tumors. However, because hemangiomas are tumors having little blood flow, it is difficult to detect hemangiomas through non-contrast imaging processes such as those using a Doppler mode or the like.

Incidentally, it is known that hemangiomas appear as a "fluttering" phenomenon in B-mode images obtained by ultrasound diagnosis apparatuses. There are various theories about what causes the fluttering phenomenon. It is safe to say that, although not having completely been elucidated, the fluttering phenomenon is one of characteristic observations from hemangiomas. However, it would be difficult, even for skilled medical doctors, to diagnose hemangiomas only from observing such fluttering in a B-mode image.

BRIEF DESCRIPTION OF THE DRAWINGS

FIG. 5 is a drawing for explaining a difference calculating process performed by image processing circuitry according to the first embodiment;

FIG. 10 is a flowchart illustrating a processing procedure in an index value calculating process according to a second embodiment;

FIG. 11 is a block diagram illustrating an exemplary configuration of an image processing apparatus according to another embodiment;

FIG. 12 is a drawing for explaining a filtering process according to yet another embodiment;

FIG. 13 is another drawing for explaining the filtering process according to said yet another embodiment.

DETAILED DESCRIPTION

An image processing apparatus according to an embodiment includes processing circuitry. The processing circuitry is configured to perform a speckle noise reducing process on each of a plurality of images that were acquired by using an ultrasound wave and are in a time series. The processing circuitry is configured to calculate an index value indicating fluttering of image signal intensities in each of multiple positions within a region of interest, on the basis of the plurality of images resulting from the speckle noise reducing process.

Exemplary embodiments of an image processing apparatus and an ultrasound diagnosis apparatus will be explained below, with reference to the accompanying drawings. The embodiments described below are not limited by the explanations below. Further, it is possible to combine each of the embodiments with any other embodiment or conventional technique, so long as no conflict occurs in the contents of the processing.

Further, in the embodiments below, an example will be explained in which the present disclosure is applied to an ultrasound diagnosis apparatus; however, possible embodiments are not limited to this example. For instance, the present disclosure is applicable not only to ultrasound diagnosis apparatuses, but also to image processing apparatuses and other medical image diagnosis apparatuses having a function of processing images. Examples of applicable image processing apparatuses include workstations and Picture Archiving Communication System (PACS) viewers. Examples of other medical image diagnosis apparatuses include opto-ultrasound diagnosis apparatuses (opto-acoustic imaging apparatuses), X-ray diagnosis apparatuses, X-ray Computed Tomography (CT) apparatuses, Magnetic Resonance Imaging (MRI) apparatuses, Single Photon Emission Computed Tomography (SPECT) apparatuses, Positron Emission computed Tomography (PET) apparatuses, SPECT-CT apparatuses in each of which a SPECT apparatus is combined with an X-ray CT apparatus, PET-CT apparatuses in each of which a PET apparatus is combined with an X-ray CT apparatus, or a group of apparatuses including any of these apparatuses.

First Embodiment

Figure 1:
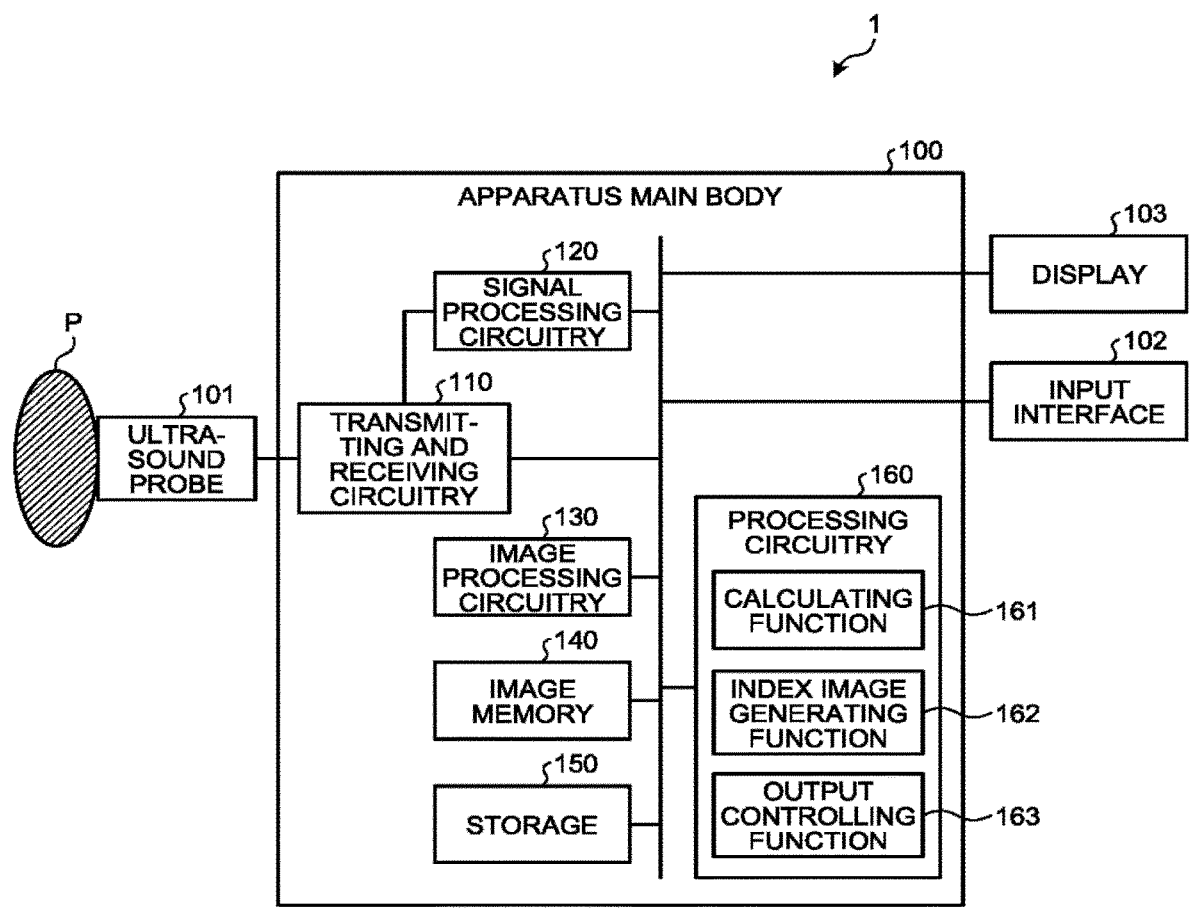
FIG. 1 is a block diagram illustrating an exemplary configuration of an ultrasound diagnosis apparatus according to a first embodiment.

FIG. 1 is a block diagram illustrating an exemplary configuration of an ultrasound diagnosis apparatus 1 according to a first embodiment. As illustrated in FIG. 1, the ultrasound diagnosis apparatus 1 according to the first embodiment includes an apparatus main body 100, an ultrasound probe 101, an input interface 102, and a display 103. The ultrasound probe 101, the input interface 102, and the display 103 are connected so as to be able to communicate with the apparatus main body 100. An examined subject (hereinafter, "patient") P is not included in the configuration of the ultrasound diagnosis apparatus 1.

The ultrasound probe 101 includes a plurality of transducer elements (e.g., piezoelectric transducer elements). Each of the plurality transducer elements is configured to generate an ultrasound wave on the basis of a drive signal supplied thereto from transmitting and receiving circuitry 110 included in the apparatus main body 100 (explained later).

Further, each of the plurality of transducer elements included in the ultrasound probe 101 is configured to receive a reflected wave from the patient P and to convert the received reflected wave into an electrical signal. Further, the ultrasound probe 101 includes matching layers provided for the transducer elements, as well as a backing member or the like that prevents ultrasound waves from propagating rearward from the transducer elements.

When an ultrasound wave is transmitted from the ultrasound probe 101 to the patient P, the transmitted ultrasound wave is repeatedly reflected on a surface of discontinuity of acoustic impedances at a tissue in the body of the patient P and is received as a reflected-wave signal (an echo signal) by each of the plurality of transducer elements included in the ultrasound probe 101. The amplitude of the received reflected-wave signal is dependent on the difference between the acoustic impedances on the surface of discontinuity on which the ultrasound wave is reflected.

When a transmitted ultrasound pulse is reflected on the surface of a moving blood flow, a cardiac wall, or the like, the reflected-wave signal is, due to the Doppler effect, subject to a frequency shift, depending on a velocity component of the moving members with respect to the ultrasound wave transmission direction.

Further, the first embodiment is applicable to any of the following situations: The ultrasound probe 101 illustrated in FIG. 1 is a one-dimensional ultrasound probe in which the plurality of piezoelectric transducer elements are arranged in a row; The ultrasound probe 101 is a one-dimensional ultrasound probe in which the plurality of piezoelectric transducer elements arranged in a row are mechanically caused to swing; and The ultrasound probe 101 is a two-dimensional ultrasound probe in which the plurality of piezoelectric transducer elements are two-dimensionally arranged in a grid formation.

The input interface 102 corresponds to a mouse, a keyboard, a button, a panel switch, a touch command screen, a foot switch, a trackball, a joystick, and/or the like. For example, the input interface 102 is configured to receive various types of setting requests from the operator of the ultrasound diagnosis apparatus 1 and to transfer the received various types of setting requests to the apparatus main body 100.

The display 103 is configured to display a Graphical User Interface (GUI) used by the operator of the ultrasound diagnosis apparatus 1 to input the various types of setting requests through the input interface 102 and to display ultrasound image data generated by the apparatus main body 100 or the like.

The apparatus main body 100 is an apparatus configured to generate the ultrasound image data on the basis of the reflected-wave signals received by the ultrasound probe 101. As illustrated in FIG. 1, the apparatus main body 100 includes the transmitting and receiving circuitry 110, signal processing circuitry 120, image processing circuitry 130, an image memory 140, storage 150, and processing circuitry 160. The transmitting and receiving circuitry 110, the signal processing circuitry 120, the image processing circuitry 130, the image memory 140, the storage 150, and the processing circuitry 160 are connected so as to be able to communicate with one another.

The transmitting and receiving circuitry 110 includes a pulse generator, a transmission delay unit, a pulser, and the like and is configured to supply the drive signal to the ultrasound probe 101. The pulse generator is configured to repeatedly generate a rate pulse used for forming a transmission ultrasound wave, at a predetermined rate frequency. Further, the transmission delay unit is configured to apply a delay period that is required to converge the ultrasound wave generated by the ultrasound probe 101 into the form of a beam and to determine transmission directionality and that corresponds to each of the piezoelectric transducer elements, to each of the rate pulses generated by the pulse generator. Further, the pulser is configured to apply the drive signal (a drive pulse) to the ultrasound probe 101 with timing based on the rate pulses. In other words, by varying the delay periods applied to the rate pulses, the transmission delay unit is able to arbitrarily adjust the transmission directions of the ultrasound waves transmitted from the surfaces of the piezoelectric transducer elements.

In this situation, the transmitting and receiving circuitry 110 has a function that is able to instantly change the transmission frequency, the transmission drive voltage, and the like, for the purpose of executing a predetermined scanning sequence on the basis of an instruction from the processing circuitry 160 (explained later). In particular, the function to change the transmission drive voltage is realized by using a linear-amplifier-type transmission circuit of which the value can be instantly switched or by using a mechanism configured to electrically switch between a plurality of power source units.

Further, the transmitting and receiving circuitry 110 includes a pre-amplifier, an Analog/Digital (A/D) converter, a reception delay unit, an adder, and the like and is configured to generate reflected-wave data by performing various types of processes on the reflected-wave signals received by the ultrasound probe 101. The pre-amplifier is configured to amplify the reflected-wave signal for each of the channels. The A/D converter is configured to perform an A/D conversion on the amplified reflected-wave signals. The reception delay unit is configured to apply a delay period required to determine reception directionality thereto. The adder is configured to generate the reflected-wave data by performing an adding process on the reflected-wave signals processed by the reception delay unit. As a result of the adding process performed by the adder, reflected components from the direction corresponding to the reception directionality of the reflected-wave signals are emphasized. A comprehensive beam for the ultrasound transmission and reception is formed according to the reception directionality and the transmission directionality.

When scanning a two-dimensional region of the patient P, the transmitting and receiving circuitry 110 causes the ultrasound probe 101 to transmit an ultrasound beam in a two-dimensional direction. Further, the transmitting and receiving circuitry 110 generates two-dimensional reflected-wave data from the reflected-wave signals received by the ultrasound probe 101. As another example, when scanning a three-dimensional region of the patient P, the transmitting and receiving circuitry 110 causes the ultrasound probe 101 to transmit an ultrasound beam in a three-dimensional direction. Further, the transmitting and receiving circuitry 110 generates three-dimensional reflected-wave data from the reflected-wave signals received by the ultrasound probe 101.

For example, the signal processing circuitry 120 is configured to generate data (B-mode data) in which the signal intensity is expressed by a degree of brightness for each sampling point, by performing a logarithmic amplification, an envelope detection process, and/or the like on the reflected-wave data received from the transmitting and receiving circuitry 110. The B-mode data generated by the signal processing circuitry 120 is output to the image processing circuitry 130.

Further, for example, from the reflected-wave data received from the transmitting and receiving circuitry 110, the signal processing circuitry 120 is configured to generate data (Doppler data) obtained by extracting, from each sampling point in the scanned region, motion information based on the Doppler effect on the moving members. More specifically, the signal processing circuitry 120 generates the data (the Doppler data) obtained by extracting moving member information such as average velocity, dispersion, power, and the like with respect to multiple points, by performing a frequency analysis to obtain velocity information from the reflected-wave data and extracting blood flows, tissues, contrast agent echo components based on the Doppler effect. In this situation, examples of the moving members include blood flows, tissues such as cardiac walls, and the contrast agent. The motion information (blood flow information) obtained by the signal processing circuitry 120 is forwarded to the image processing circuitry 130 and is displayed on the display 103 in color as an average velocity image, a dispersion image, a power image, or an image combining any of these images.

The image processing circuitry 130 is configured to generate the ultrasound image data from the data generated by the signal processing circuitry 120. The image processing circuitry 130 is configured to generate B-mode image data in which intensities of the reflected waves are expressed by degrees of brightness, from the B-mode data generated by the signal processing circuitry 120. Further, the image processing circuitry 130 is configured to generate Doppler image data expressing the moving member information from the Doppler data generated by the signal processing circuitry 120. The Doppler image data is velocity image data, dispersion image data, power image data, or image data combining any of these types of image data.

In this situation, generally speaking, the image processing circuitry 130 converts (by performing a scan convert process) a scanning line signal sequence from an ultrasound scan into a scanning line signal sequence in a video format used by, for example, television and generates display-purpose ultrasound image data. More specifically, the image processing circuitry 130 generates the display-purpose ultrasound image data by performing a coordinate transformation process compliant with the ultrasound scanning mode used by the ultrasound probe 101. Further, as various types of image processing processes besides the scan convert process, the image processing circuitry 130 performs, for example, an image processing process (a smoothing process) to re-generate a brightness average value image, an image processing process (an edge enhancement process) that uses a differential filter inside an image, or the like, by using a plurality of image frames resulting from the scan convert process. Also, the image processing circuitry 130 combines additional information (text information of various parameters, scale graduations, body marks, and the like) with the ultrasound image data.

In other words, the B-mode data and the Doppler data are each ultrasound image data before the scan convert process. The data generated by the image processing circuitry 130 is the display-purpose ultrasound image data after the scan convert process. When the signal processing circuitry 120 has generated three-dimensional data (three-dimensional B-mode data and three-dimensional Doppler data), the image processing circuitry 130 generates volume data by performing a coordinate transformation process in accordance with the ultrasound scanning mode used by the ultrasound probe 101. Further, the image processing circuitry 130 generates the display-purpose two-dimensional image data by performing any of various types of rendering processes on the volume data.

The image memory 140 is a memory configured to store therein the display-purpose images generated by the image processing circuitry 130. Further, the image memory 140 is also capable of storing therein any of the data generated by the signal processing circuitry 120. After a diagnosis process, for example, the operator is able to invoke any of the B-mode data and the Doppler data stored in the image memory 140. The invoked B-mode data and Doppler-data can serve as display-purpose ultrasound image data after being routed through the image processing circuitry 130. When the description of the present embodiment simply uses the term "image", not only display-purpose images in which colors are assigned to the pixels, but also data sequences (which may be referred to as "image data") in which coordinates of the pixels are kept in correspondence with pixel values (signal values) may be referred to thereby.

The storage 150 is configured to store therein control programs for performing ultrasound transmissions and receptions, image processing processes, and display processes as well as various types of data such as diagnosis information (e.g., patient's IDs, medical doctors' observations), diagnosis protocols, various types of body marks, and the like. Further, the storage 150 may be used, as necessary, for saving therein any of the image data stored in the image memory 140 and the like. Further, the data stored in the storage 150 may be transferred to an external apparatus via a communication-purpose interface (not illustrated).

The processing circuitry 160 is configured to control the overall processes performed by the ultrasound diagnosis apparatus 1. More specifically, the processing circuitry 160 is configured to control processes performed by the transmitting and receiving circuitry 110, the signal processing circuitry 120, and the image processing circuitry 130, on the basis of the various types of setting requests input by the operator via the input interface 102 and the various types of control programs and various types of data read from the storage 150. Further, the processing circuitry 160 is configured to exercise control so that the display 103 displays any of the display-purpose ultrasound image data stored in the image memory 140.

Further, as illustrated in FIG. 1, the processing circuitry 160 executes a calculating function 161, an index image generating function 162, and an output controlling function 163. The calculating function 161 is an example of a calculating unit. The index image generating function 162 is an example of an image generating unit. The output controlling function 163 is an example of an output controlling unit.

In this situation, for example, the processing functions executed by the constituent elements of the processing circuitry 160 illustrated in FIG. 1, namely, the calculating function 161, the index image generating function 162, and the output controlling function 163, are each recorded in a storage device (e.g., the storage 150) of the ultrasound diagnosis apparatus 1 in the form of a computer-executable program. The processing circuitry 160 is a processor configured to realize the functions corresponding to the programs by reading and executing the programs from the storage device. In other words, the processing circuitry 160 that has read the programs has the functions illustrated in the processing circuitry 160 in FIG. 1. The processing functions executed by the calculating function 161, the index image generating function 162, and the output controlling function 163 will be explained later.

Incidentally, it is known that hemangiomas, which are a type of benign tumors, appear as a "fluttering" phenomenon in B-mode images obtained by the ultrasound diagnosis apparatus 1. There are various theories about what causes the fluttering phenomenon. It is safe to say that, although not having completely been elucidated, the fluttering phenomenon is one of characteristic observations from hemangiomas.

Figure 2:
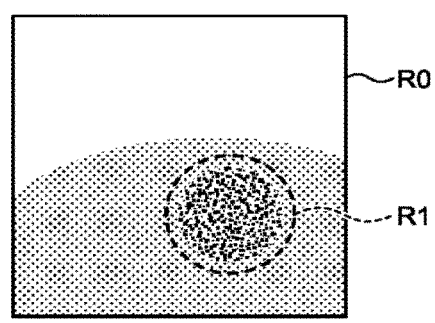
FIG. 2 is a drawing for explaining a fluttering phenomenon exhibited by a hemangioma.

FIG. 2 is a drawing for explaining the fluttering phenomenon exhibited by a hemangioma. FIG. 2 illustrates a B-mode image taken of the liver of the patient P. As illustrated in FIG. 2, the hemangioma is rendered as a shadow (a region rendered with brightness levels that are different from those for other tissues) in a region R1 within a region of interest R0 set in the B-mode image. The shadow of the hemangioma has a characteristic of being exhibited as spatial and temporal fluttering. In other words, the shadow of the hemangioma is exhibited as "spatial fluttering" where parts having higher degrees of brightness are present while being mixed with parts having lower degrees of brightness within the region R1, and also, as "temporal fluttering" where the degree of brightness in the same position chronologically rises and falls.

However, in some situations, it may be difficult to diagnose hemangiomas only from observing such fluttering in a B-mode image. To cope with this situation, the ultrasound diagnosis apparatus 1 according to the first embodiment executes the processing functions explained below, to quantitatively evaluate such fluttering in images or to emphasize the position of the fluttering.

In the embodiments described below, an example will be explained in which the fluttering phenomenon of a hemangioma rendered in B-mode images is evaluated; however, possible embodiments are not limited to this example. For instance, the present disclosure makes it possible to quantitatively evaluate changes not only of hemangiomas but of any tissue exhibiting such a fluttering phenomenon in images. Further, the present disclosure also makes it possible to evaluate the fluttering phenomenon not only in B-mode images, but also in other types of ultrasound images such as Doppler images and medical images taken by other types of medical image diagnosis apparatuses.

In the ultrasound diagnosis apparatus 1 according to the first embodiment, the image processing circuitry 130 is configured to perform a speckle noise reducing process on each of a plurality of images that were acquired by using an ultrasound wave and are in a time series. The calculating function 161 is configured to calculate an index value indicating fluttering of image signal intensities in each of multiple positions within a region of interest, on the basis of the plurality of images resulting from the speckle noise reducing process. As a result, the ultrasound diagnosis apparatus 1 is able to quantitatively evaluate the fluttering in the images.

Further, for example, in the ultrasound diagnosis apparatus 1 according to the first embodiment, the index image generating function 162 is configured to generate a parametric image on the basis of the index values with respect to the multiple positions within the region of interest. As a result, the operator is able to browse the extent of fluttering in the image.

Figure 3:
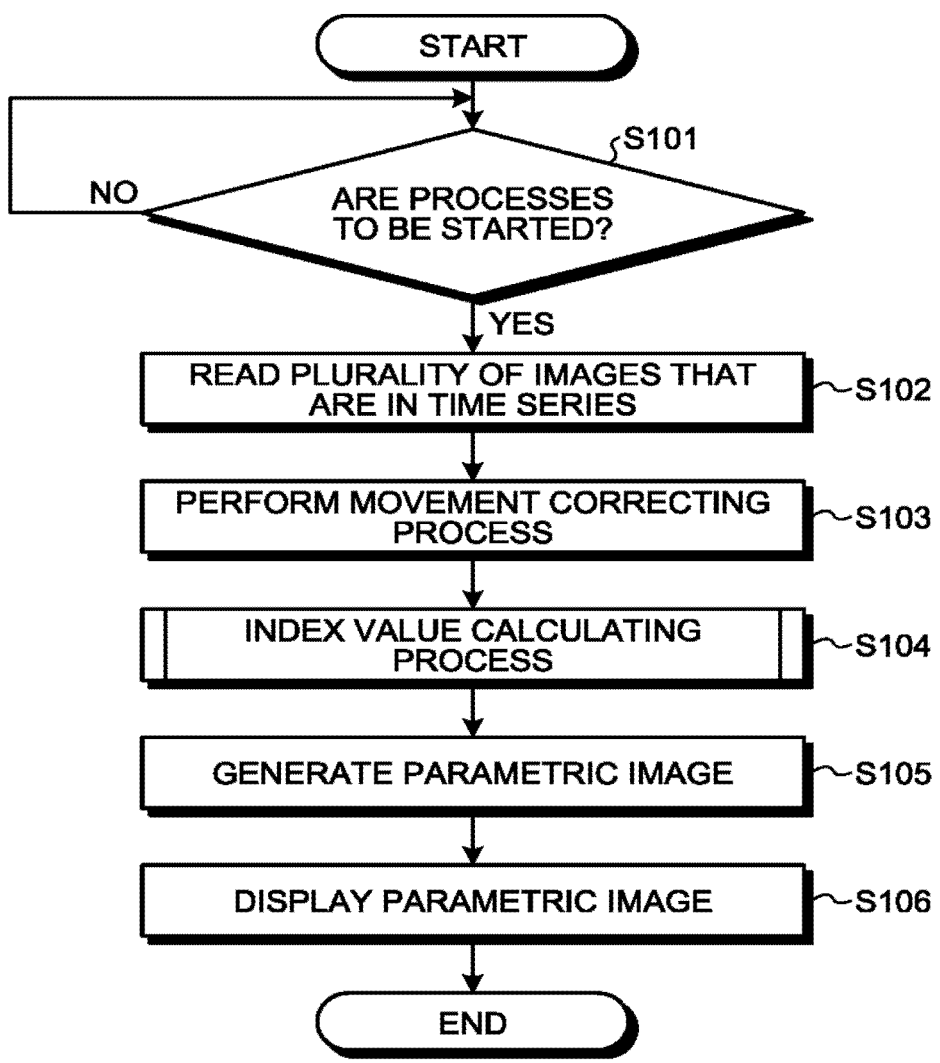
FIG. 3 is a flowchart illustrating a processing procedure performed by an ultrasound diagnosis apparatus according to the first embodiment.
Figure 4:
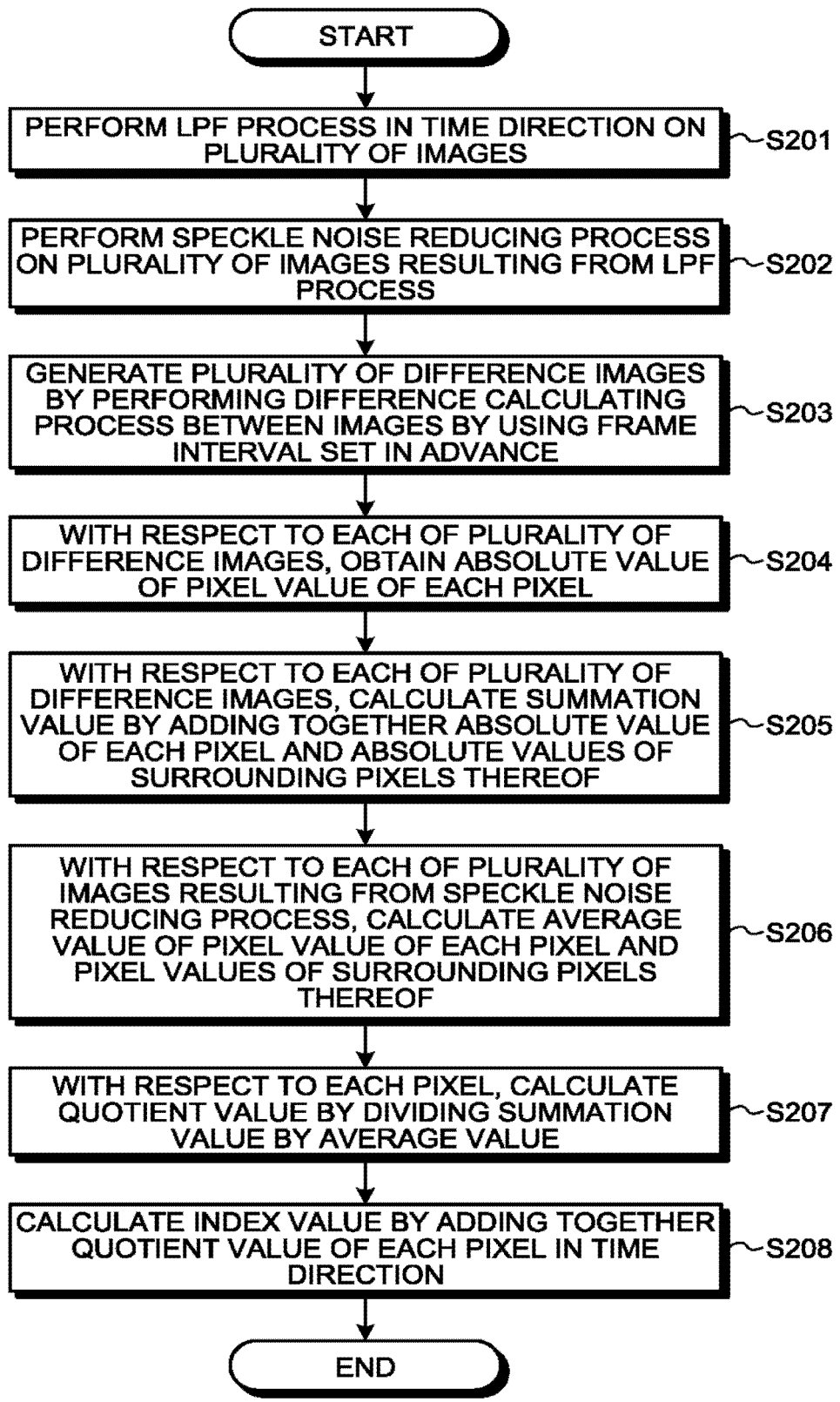
FIG. 4 is a flowchart illustrating a processing procedure in an index value calculating process according to the first embodiment.

A processing procedure performed by the ultrasound diagnosis apparatus 1 according to the first embodiment will be explained, with reference to FIGS. 3 and 4. FIG. 3 is a flowchart illustrating a processing procedure performed by the ultrasound diagnosis apparatus 1 according to the first embodiment. FIG. 4 is a flowchart illustrating a processing procedure in an index value calculating process according to the first embodiment. For example, the processing procedure illustrated in FIG. 3 is started when an instruction is received from the operator indicating that a parametric image be displayed. The processing procedure illustrated in FIG. 4 corresponds to the process at step S104 in FIG. 3.

Figure 6:
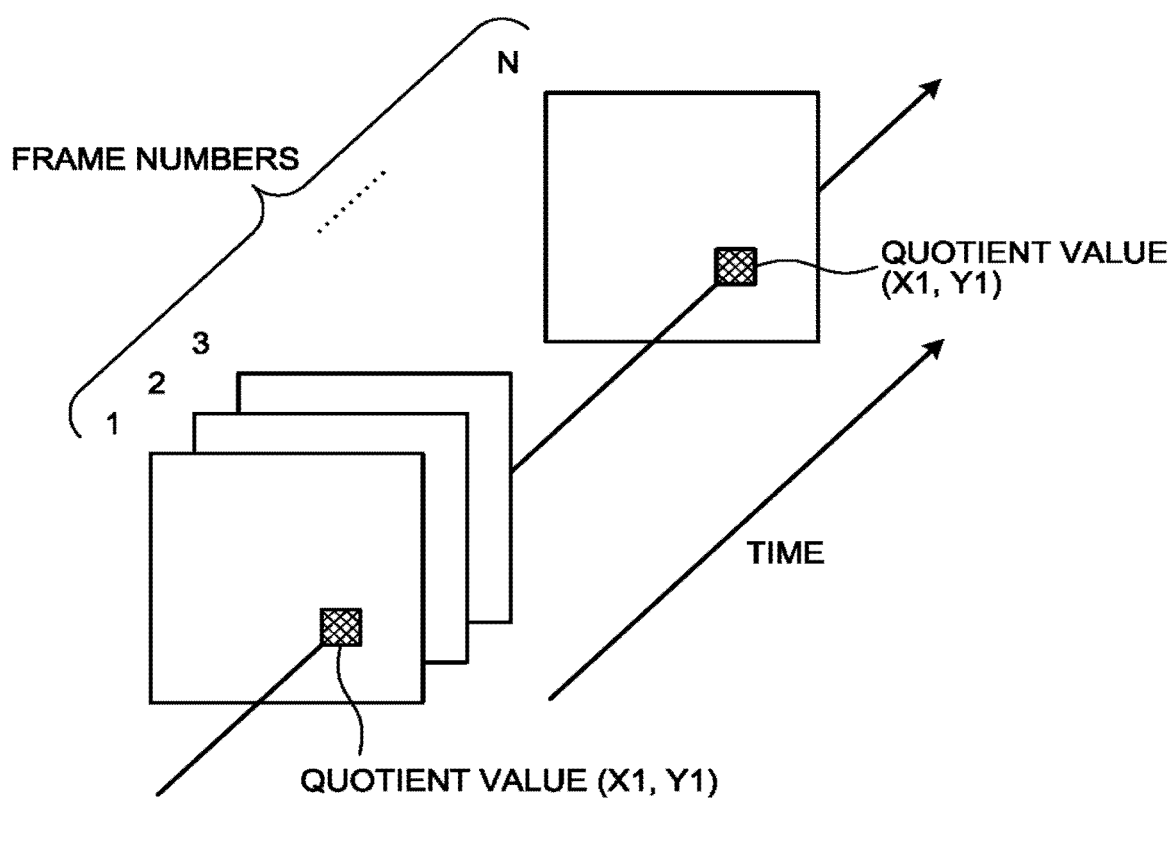
FIG. 6 is a drawing for explaining a process performed by a calculating function according to the first embodiment.
Figure 7:
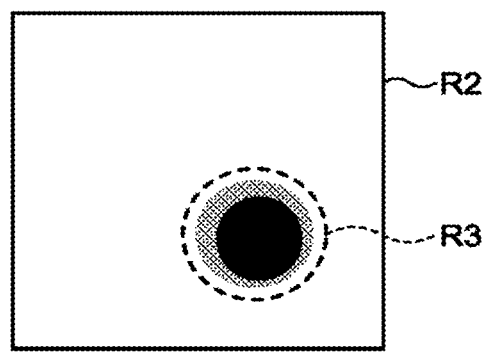
FIG. 7 is a drawing for explaining a process performed by an index image generating function according to the first embodiment.

Further, the following explanations will refer to FIGS. 5 to 7. FIG. 5 is a drawing for explaining a difference calculating process performed by the image processing circuitry 130 according to the first embodiment. FIG. 6 is a drawing for explaining a process performed by the calculating function 161 according to the first embodiment. FIG. 7 is a drawing for explaining a process performed by the index image generating function 162 according to the first embodiment.

At step S101, the processing circuitry 160 judges whether or not the processes are to be started. For example, when an instruction is received from the operator indicating that a parametric image be displayed, the processing circuitry 160 determines that the processes are to be started (step S101: Yes) and starts the processes at step S102 and thereafter. On the contrary, when the processes are not to be started (step S101: No), the processes at step S102 and thereafter are not started, and the processing functions are in a standby state.

When the judgment result at step S101 is in the affirmative, the image processing circuitry 130 reads a plurality of images that are in a time series at step S102. For example, the image processing circuitry 130 reads pieces of B-mode image data corresponding to a plurality of temporal phases and being arranged in a time series, from the image memory 140. In a specific example, the image processing circuitry 130 reads N pieces of B-mode image data in the first to N-th frames, from the image memory 140 (where N is a natural number). Further, with respect to the processes described below, the processing target may be pieces of B-mode image data corresponding to the entire scanned region on which the ultrasound scan was performed or may be only the pieces of image data of the region of interest. Further, in the processes described below, an example will be explained in which the plurality of images corresponding to the N consecutive frames serve as the processing target; however, possible embodiments are not limited to this example. For instance, the processing target may be images obtained by thinning out every other frame from the images in the first to the N-th frames. The B-mode image data is a non-contrast image taken without using contrast agent.

In the following sections, an example will be explained in which the N pieces of B-mode image data have already been taken and stored in the image memory 140 in advance; however, possible embodiments are not limited to this example. For instance, the image processing circuitry 130 may obtain the generated N pieces of B-mode image data in a real-time manner. In that situation, for example, after step S101, the operator performs an ultrasound scan to obtain N frames by using the ultrasound probe 101. After that, the image processing circuitry 130 is able to generate the pieces of B-mode image data corresponding to the N frames, on the basis of the pieces of B-mode data corresponding to the N frames acquired in the ultrasound scan.

At step S103, the image processing circuitry 130 performs a movement correcting process to correct movements between images on the plurality of images. For example, the read N pieces of B-mode image data include movements between images (positional shifts) caused by the operator not holding the imaging device steadily or by body movements (e.g., heartbeats). For this reason, the image processing circuitry 130 identifies the positional shifts in the images by performing a tracking process on the N pieces of B-mode image data. After that, the image processing circuitry 130 generates a series of pieces of B-mode image data containing no positional shifts in the time direction, by correcting the identified positional shifts in the images.

At step S104, an index value calculating process is performed. The index value calculating process is performed by the image processing circuitry 130 and the calculating function 161. The process performed at steps S201 through S208 as the index value calculating process will be explained, with reference to FIG. 4. The process at steps S201 through S203 corresponds to a process of emphasizing temporal fluttering (fluctuations in the pixel values). Further, the process at steps S204 through S208 corresponds to a process of calculating index values.

At step S201, the image processing circuitry 130 performs a Low-Pass Filter (LPF) process in the time direction (the frame direction) on the plurality of images. For example, the image processing circuitry 130 applies an LPF such as a moving average filter, a median filter, or the like to pixel values that are arranged in the frame direction and of which the quantity is equal to N, with respect to the pixels in the B-mode images of which the quantity is equal to N. As a result, the image processing circuitry 130 is able to reduce radio frequency noise such as spike noise in the time direction, within the image signal intensities in the time direction. In this situation, the pixel values (brightness values) serve as an example of the image signal intensities.

At step S202, the image processing circuitry 130 performs a speckle noise reducing process on the plurality of images resulting from the LPF process. For example, the image processing circuitry 130 applies, in the spatial direction, a median filter to the B-mode images of which the quantity is equal to N. As a result, the image processing circuitry 130 is able to reduce spike noise and speckle noise in the spatial direction. The image processing circuitry 130 forwards the B-mode images of which the quantity is equal to N and on which the speckle noise reducing process has been performed, to the processing circuitry 160.

At step S203, the image processing circuitry 130 generates a plurality of difference images, by performing a difference calculating process between images by using a frame interval that is set in advance.

In this situation, it is considered that the image signal intensities of the plurality of B-mode images in the time series have mixed therein a fluttering component as a background (hereinafter, "background component"), in addition to a fluttering component caused by the hemangioma (hereinafter, "hemangioma component"). The fluttering as the background includes fluttering caused by various factors such as, for example, fluttering caused by tissues of the liver, fluttering caused by manipulations of the operator, fluttering caused by capability of the apparatus, fluttering caused by speckles, and the like. Thus, the image processing circuitry 130 performs the difference calculating process for the purpose of eliminating, from the image signal intensities of the B-mode images, any fluttering component having a frequency different from the frequency of the fluttering caused by the hemangioma.

The difference calculating process performed by the image processing circuitry 130 according to the first embodiment will be explained, with reference to FIG. 5. FIG. 5 illustrates a process of generating a difference image (bottom) from a B-mode image (top) by performing the difference calculating process. More specifically, the top section of FIG. 5 illustrates a chronological fluctuation in the pixel value of a certain pixel in B-mode images. Further, the bottom section of FIG. 5 illustrates a chronological fluctuation in the pixel value (the difference value) of the certain pixel in difference images. In FIG. 5, M denotes a natural number. Further, M−4, M−3, M−2, M−1, M, M+1, and M+2 are each a value included in the range from 1 to N.

As illustrated in FIG. 5, the image signal intensities of the plurality of B-mode images in the time series include a hemangioma component (the solid line in the top section of FIG. 5) and a background component (the broken line in the top section of FIG. 5). In this situation, when one cycle of the background component corresponds to four frames, the background component in the M-th frame and the background component in the (M−4)-th frame are substantially equal to each other. Thus, the image processing circuitry 130 cancels out the background components by subtracting the pixel value in the (M−4)-th frame from the pixel value in the M-th frame. As a result, the image processing circuitry 130 emphasizes the hemangioma component in the M-th frame.

Similarly, the image processing circuitry 130 emphasizes the hemangioma component in the (M+1)-th frame by subtracting the pixel value in the (M−3)-th frame from the pixel value in the (M+1)-th frame. Further, the image processing circuitry 130 emphasizes the hemangioma component in the (M+2)-th frame by subtracting the pixel value in the (M−2)-th frame from the pixel value in the (M+2)-th frame.

In this manner, the image processing circuitry 130 performs the difference calculating process between the B-mode images by using a frame interval of "4". More specifically, with respect to each of the pixels in the B-mode images of which the quantity is equal to N, the image processing circuitry 130 calculates a difference value from the pixel value in the same position four frames ago (the bottom section of FIG. 5). After that, by assigning the calculated difference value to each of the pixels, the image processing circuitry 130 generates difference images of which the quantity is equal to N−4. Subsequently, the image processing circuitry 130 forwards the generated difference images of which the quantity is equal to N−4, to the processing circuitry 160. In this situation, the frame interval is set in advance (preset) in accordance with the image taking site and the capability of the apparatus (the type of the ultrasound probe 101, the scan sequence, and the like).

The illustration in FIG. 5 is merely an example, and possible embodiments are not limited to this example. For instance, although FIG. 5 illustrates the example in which the frame interval is "4", the value of the frame interval is not limited to the one in this example. It is possible to set any arbitrary value.

Further, although FIG. 5 illustrates the example in which the frame interval is preset, possible embodiments are not limited to this example. For instance, the frame interval may be changed by the operator via the input interface 102. In that situation, the operator designates (changes) the frame interval while browsing the parametric image displayed as a result of the process explained below. After that, the image processing circuitry 130 performs the difference calculating process by using the frame interval designated by the operator. When the operator changes the frame interval, for example, the chart in the top section of FIG. 5 may be displayed on the display 103. Further, the parameter designated by the operator does not necessarily have to be the frame interval, but may be any other parameter that can be converted into a frame interval, such as the frequency, the cycle, or the like.

Returning to the description of FIG. 4, at step S204, with respect to each of the plurality of difference images, the calculating function 161 obtains the absolute value of the pixel value of each of the pixels. In this situation, the difference value of each of the pixels in the difference images may be a negative value. For this reason, the calculating function 161 obtains the absolute value of the difference value of each of the pixels. As a result, it is possible to express the fluttering caused by the hemnangioma included in the difference images, by using positive values.

At step S205, with respect to each of the plurality of difference images, the calculating function 161 calculates a summation value obtained by adding together the absolute value of each of the pixels and absolute values of surrounding pixels thereof. For example, by using a small region (a kernel), the calculating function 161 adds together the absolute value of each of the pixels and the absolute values of the surrounding pixels thereof.

As one example, let us discuss a situation in which a small region having a 3×3 rectangular shape is used. In that situation, the calculating function 161 sets a small region in each of the difference images in such a manner that the center of the small region corresponds to a pixel of interest. At this time, present in the small region are the pixel of interest and eight surrounding pixels that are positioned in the surroundings of the pixel of interest. The calculating function 161 calculates, as a summation value of the pixel of interest, a sum of the absolute value of the pixel of interest and the absolute values of the eight surrounding pixels.

In this manner, with respect to each of the pixels in the plurality of difference images, the calculating function 161 calculates a summation value with the surrounding pixels thereof. Although the example was explained in which the region having the 3×3 rectangular shape is used as the small region, possible embodiments are not limited to this example. It is possible to use a region having any arbitrary shape and size.

At step S206, with respect to each of the plurality of images resulting from the speckle noise reducing process, the calculating function 161 calculates an average value of the pixel value of each of the pixels and the pixel values of the surrounding pixels thereof. For example, by using a small region, the calculating function 161 calculates the average value of the pixel value of each of the pixels and the pixel values of the surrounding pixels thereof.

As one example, let us discuss a situation in which a small region having a 3×3 rectangular shape is used. In that situation, the calculating function 161 sets a small region in each of the B-mode images in such a manner that the center of the small region corresponds to a pixel of interest. In that situation, present in the small region are the pixel of interest and eight surrounding pixels that are positioned in the surroundings of the pixel of interest. The calculating function 161 calculates an average value of the pixel value of the pixel of interest and the pixel values of the eight surrounding pixels.

In this manner, with respect to each of the pixels in the plurality of B-mode images, the calculating function 161 calculates an average value with the surrounding pixels thereof. Although the example was explained in which the region having the 3×3 rectangular shape is used as the small region, possible embodiments are not limited to this example. It is possible to use a region having any arbitrary shape and size.

At step S207, for each of the pixels, the calculating function 161 calculates a quotient value obtained by dividing the summation value by the average value. For example, the calculating function 161 divides the summation value of each of the pixels in the M-th frame by the average value of the pixel in the M-th frame. In this situation, the summation value is the value calculated in the process at step S205. The average value is the value calculated in the process at step S206. Thus, the calculating function 161 calculates the quotient value of each of the pixels for each of the frames (the temporal phases).

At step S208, the calculating function 161 calculates an index value by adding together, in the time direction, the quotient values of each of the pixels. For example, the calculating function 161 calculates the index value by adding together the quotient values of a pixel in mutually the same position in the plurality of frames.

An example of the process performed by the calculating function 161 according to the first embodiment will be explained with reference to FIG. 6. In FIG. 6, "Quotient Value (X1,Y1)" denotes the quotient value in a pixel position (X1,Y1). Further, "Index Value (X1,Y1)" denotes the index value in the pixel position (X1,Y1). With reference to FIG. 6, an example will be explained in which an index value of each of the pixels contained in the region of interest R0 in FIG. 2 is to be calculated.

As illustrated in the top section of FIG. 6, the calculating function 161 adds together quotient values (X1,Y1) in mutually the same position in the first to the N-th frames. In this situation, it is safe to say that the summation value is a value obtained by adding together the fluctuation in the time direction in each frame, with respect to the frames of which the quantity is equal to N. Accordingly, the calculating function 161 outputs the summation value (a total) as an index value (X1,Y1) indicating fluttering corresponding to the N frames (the bottom section of FIG. 6).

In this manner, with respect to each of the pixels (the positions), the calculating function 161 calculates the index value indicating fluttering in the N-th frame, on the basis of the B-mode images in the first to the N-th frames of which the quantity is equal to N. In this situation, each of the index values indicates fluttering corresponding to the N frames in the past.

The illustration in FIG. 6 is merely an example, and possible embodiments are no limited to this example. For instance, FIG. 6 illustrates the example in which the partial region of the B-mode images is set as the region of interest R0; however, possible embodiments are not limited to this example. For instance, when the entire scanned region of the B-mode images is set as the region of interest R0, the calculating function 161 is able to calculate an index value of each of the pixels contained in the entire scanned region.

Further, for example, although FIG. 6 illustrates the example in which the total of the quotient values in mutually the same position in the N frames is calculated as the index value, possible embodiments are not limited to this example. For instance, the calculating function 161 may calculate a statistical value of the quotient values in mutually the same position in the N frames, as an index value. In other words, the calculating function 161 is configured to calculate one selected from between the total and a statistical value of the quotient values of each of the pixels in the plurality of images as the index value. As the statistical value, for example, an average value, a median value, a standard deviation, a variance, a sum of squares, or the like may be used.

Returning to the description of FIG. 3, at step S105, the index image generating function 162 generates a parametric image. For example, the index image generating function 162 generates the parametric image by assigning a color corresponding to the magnitude of each of the index values output by the calculating function 161, to the pertinent pixel (position).

An example of the process performed by the index image generating function 162 according to the first embodiment will be explained with reference to FIG. 7. FIG. 7 illustrates an example of the parametric image generated by the index image generating function 162. With reference to FIG. 7, an example will be explained in which an index value is calculated for each of the pixels contained in the region of interest R0 illustrated in FIG. 2.

As illustrated in FIG. 7, the index image generating function 162 generates a parametric image of a region R2 corresponding to the region of interest R0 illustrated in FIG. 2. The parametric image is obtained by assigning a color (degrees of hue, lightness, chroma, and the like) corresponding to the magnitude of the index value of each of the pixels contained in the region of interest R0 to the pertinent position in the region R2. In other words, the degrees of darkness/lightness of the colors rendered in a region R3 within the region R2 are results of emphasizing the shadow of the fluttering in the region R1 in FIG. 1.

The illustration in FIG. 7 is merely an example, and possible embodiments are not limited to this example. For instance, FIG. 7 illustrates the example in which a partial region of the B-mode images is set as the region of interest R0; however, possible embodiments are not limited to this example. For instance, when the entire scanned region of the B-mode images is set as the region of interest R0, the index image generating function 162 is able to generate a parametric image of the region corresponding to the entire scanned region.

At step S106, the output controlling function 163 displays the parametric image. For example, the output controlling function 163 causes the display 103 to display the parametric image generated by the index image generating function 162. After that, the processing circuitry 160 ends the process.

The processing procedures illustrated in FIGS. 3 and 4 are merely examples, and possible embodiments are not limited to the processing procedures illustrated in the drawings. For example, the LPF process at step S201 and the speckle noise reducing process at step S202 do not necessarily have to be performed. Further, for example, the order in which the LPF process at step S201 and the speckle noise reducing process at step S202 may be exchanged with each other.

Further, for instance, although FIG. 3 illustrates the example in which the parametric image is displayed alone, possible embodiments are not limited to this example. For instance, the output controlling function 163 may display the parametric image together with another medical image at the same time. In one example, the output controlling function 163 may display the parametric image illustrated in FIG. 7 so as to be superimposed on the B-mode image illustrated in FIG. 2 or so as to be positioned next to the B-mode image illustrated in FIG. 2.

Further, for instance, although FIG. 3 illustrates the example of an output mode in which the parametric image is displayed, possible embodiments are not limited to this example. For instance, the output controlling function 163 may output a representative value of the index values. In that situation, the calculating function 161 calculates a representative value for a measured region, on the basis of the index values in multiple positions within the measured region corresponding to at least a part of the region of interest. For example, when the operator sets the region R3 in FIG. 7 as a measured region, the calculating function 161 calculates a representative value by using the index values of the pixels in the region R3. In this situation, the representative value is, for example, a statistical value such as an average value, a median value, a maximum value, a minimum value, or the like. Further, the output controlling function 163 causes the display 103 to display the representative value for the region R3 calculated by the calculating function 161.

Further, for example, the output controlling function 163 may display a histogram of the index values. The histogram may be, for example, a chart in which the vertical axis expresses frequency (the number of pixels), while the horizontal axis expresses magnitudes of the index value. When fluttering is detected, the chart of the histogram is shifted sideways, as a whole, from a histogram corresponding to a time when no fluttering is detected.

In other words, the output controlling function 163 is able to output information by using an output mode selected, as appropriate, from among the parametric image, the representative value, the histogram, and the like. Further, the output destination to which the information is output by the output controlling function 163 is not limited to the display 103. For example, the output controlling function 163 may store the information to be output into the storage 150 or may transmit the information to an external apparatus.

Further, for example, FIG. 4 illustrates the example in which, as the index value, the summation value is calculated by adding together the quotient values of each of the pixels in the time direction; however, possible embodiments are not limited to this example. For instance, the quotient values calculated at step S207 are also considered as values indicating fluttering of the image signal intensities in multiple positions. For this reason, the calculating function 161 may output the quotient values calculated at step S207 as index values. In that situation, the process at step S208 does not have to be performed.

As explained above, in the ultrasound diagnosis apparatus 1 according to the first embodiment, the image processing circuitry 130 is configured to perform the speckle noise reducing process on each of the plurality of images that were acquired by using the ultrasound wave and are in the time series. The calculating function 161 is configured to calculate the index value indicating the fluttering of the image signal intensities in each of the multiple positions within the region of interest, on the basis of the plurality of images resulting from the speckle noise reducing process. As a result, the ultrasound diagnosis apparatus 1 is able to quantitatively evaluate the fluttering in the images.

Further, for example, as illustrated in FIG. 2, the operator (a medical doctor) may find a shadow (the region R1) in the B-mode images. In that situation, the operator causes the display 103 to display the parametric image, by using the ultrasound diagnosis apparatus 1 according to the first embodiment. In this situation, when the shadow is emphasized by using colors (brightness values) at a predetermined level or higher, as illustrated in the region R3 in FIG. 7, the operator is able to learn that the site has fluttering in the time direction. As a result, the operator is able to determine that the shadow in the B-mode images represents a hemangioma. Consequently, it is possible to easily and conveniently discriminate hemangiomas, without performing the judgment process that uses a needle puncture or administration of a contrast agent.

Further, for example, B-mode images may render fluttering only in the spatial direction. For example, spatial fluttering may be exhibited due to speckles. In that situation, it would be difficult to judge whether or not a hemangioma is present only by observing the fluttering in the images. However, because the ultrasound diagnosis apparatus 1 according to the first embodiment is able to detect the fluttering in the time direction without detecting such fluttering that occurs only in the spatial direction, it is possible to accurately discriminate hemangiomas.

Further, the fluttering component as the background (the background component) has a small impact on the index values when the B-mode images have high degrees of brightness, but has a large impact on the index values when the B-mode images have low degrees of brightness. Accordingly, when a site (e.g., the liver) having relatively low degrees of brightness is observed, an impact of the background component could be an issue. However, the ultrasound diagnosis apparatus 1 according to the first embodiment is configured to calculate the index values after eliminating, from the image signal intensities, any fluttering component having a frequency different from the frequency of the fluttering. Consequently, the ultrasound diagnosis apparatus 1 is able to accurately evaluate the fluttering in the time direction, even from a site having relatively low degrees of brightness.

Further, for example, the ultrasound diagnosis apparatus 1 according to the first embodiment is configured to calculate the index value indicating the fluttering of the image signal intensities in each of the multiple positions within the region of interest with respect to each of the plurality of temporal phases, on the basis of each of the plurality of images that were acquired by using the ultrasound wave and are in the time series. Further, the ultrasound diagnosis apparatus 1 is configured to calculate one selected from between the sum and the statistical value of the index values corresponding to the plurality of temporal phases, with respect to each of the multiple positions within the region of interest. With these arrangements, the ultrasound diagnosis apparatus 1 is able to quantitatively evaluate the fluttering in the images.

A Modification Examples of the First Embodiment

In the first embodiment, the example is explained in which the frame interval used in the difference calculating process is set in advance. However, it is also possible to automatically determine the frame interval.

For example, the image processing circuitry 130 may determine a frame interval in accordance with the frequency of fluttering of image signal intensities included in a region different from a measured region within a region of interest. Further, the image processing circuitry 130 performs a difference calculating process by using the determined frame interval.

Figure 8:
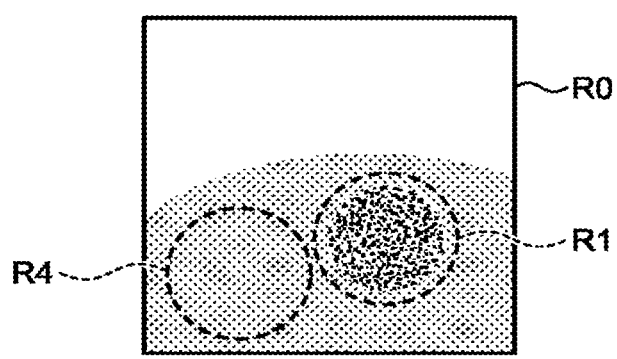
FIG. 8 is a drawing for explaining a difference calculating process performed by the image processing circuitry according to a modification example of the first embodiment.
Figure 9:
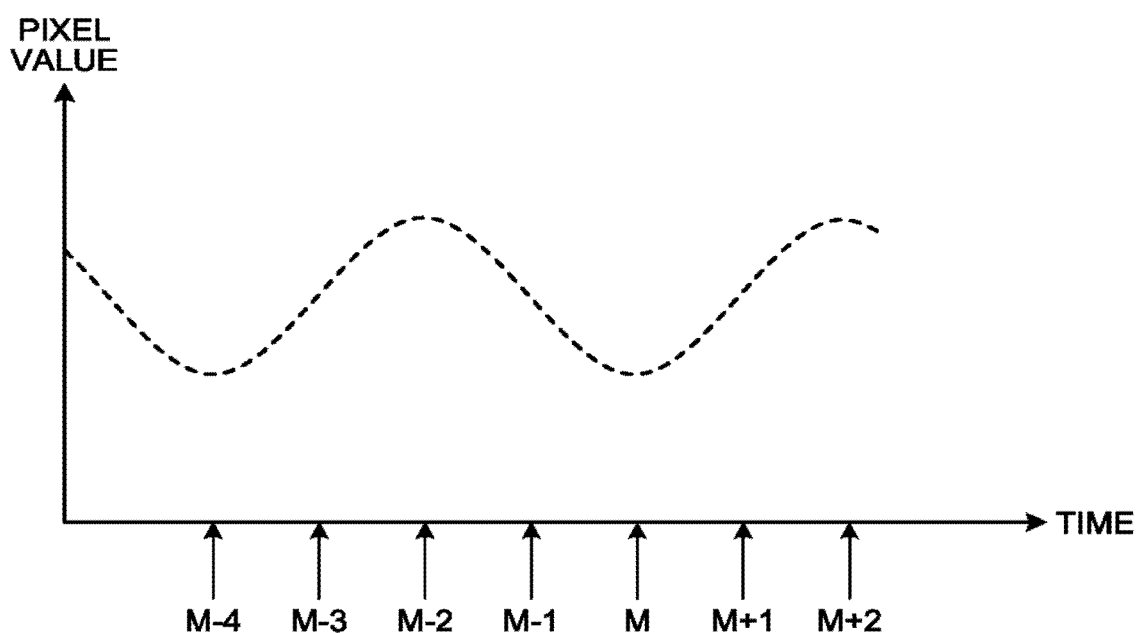
FIG. 9 is another drawing for explaining the difference calculating process performed by the image processing circuitry according to the modification example of the first embodiment.

The difference calculating process performed by the image processing circuitry 130 according to a modification example of the first embodiment will be explained, with reference to FIGS. 8 and 9. FIGS. 8 and 9 are drawings for explaining the difference calculating process performed by the image processing circuitry 130 according to the modification example of the first embodiment. FIG. 8 illustrates a B-mode image taken of the liver of the patient P. FIG. 9 illustrates a chronological fluctuation in the pixel value of a certain pixel in B-mode images.

In the example in FIG. 8, the operator sets a region R4 in the region of interest R0. The region R4 is a region in which liver tissues are rendered and that is different from the region R3 (the measured region) exhibiting the shadow. In other words, the chronological fluctuations in the pixel values in the region R4 include only the background component, as illustrated in FIG. 9.

Accordingly, the image processing circuitry 130 calculates the frequency (or the cycle) of the background component from the chronological fluctuation in the pixel value illustrated in FIG. 9. After that, the image processing circuitry 130 determines a frame interval in accordance with the calculated frequency. In the example illustrated in FIG. 9, the image processing circuitry 130 determines the frame interval to be "4". After that, the image processing circuitry 130 performs the difference calculating process by using the determined frame interval "4". Because the details of the difference calculating process are the same as those explained with reference to FIG. 5, the explanation thereof will be omitted.

With these arrangements, the ultrasound diagnosis apparatus 1 according to the modification example of the first embodiment is able to automatically determine the frame interval to be used in the difference calculating process. In this situation, the region R4 illustrated in FIG. 8 may be set manually by the operator or may be set automatically. Further, when the operator changes the frame interval, the chart in FIG. 9 may be displayed on the display 103, for example.

Second Embodiment

In the first embodiment above, the example is explained in which the index values each indicating the fluttering in the time direction are calculated after eliminating the background component of the fluttering in the time direction; however, possible embodiments are not limited to this example. For instance, the process of eliminating the background component does not necessarily have to be performed. Accordingly, as a second embodiment, an example will be explained in which the ultrasound diagnosis apparatus 1 does not perform the process of eliminating the background component.

The ultrasound diagnosis apparatus 1 according to the second embodiment has the same configuration as that of the ultrasound diagnosis apparatus 1 illustrated in FIG. 1, except that a part of the index value calculating process illustrated in FIG. 3 is different. Thus, the second embodiment will be explained while a focus is placed on differences from the first embodiment. Explanations about the configurations that were explained in the first embodiment will be omitted.

A processing procedure performed by the ultrasound diagnosis apparatus 1 according to the second embodiment will be explained with reference to FIG. 10. FIG. 10 is a flowchart illustrating a processing procedure in an index value calculating process according to the second embodiment. The processing procedure illustrated in FIG. 10 corresponds to the process at step S104 in FIG. 3. Because the processes at steps S301 and S302 in FIG. 10 are the same as the processes at steps S201 and S202 in FIG. 4, the explanations thereof will be omitted.

At step S303, the calculating function 161 calculates a standard deviation of the pixel value in the time direction, for each of the pixels (the positions). For example, for each of the pixels, the calculating function 161 calculates a standard deviation of the pixel values of the same pixel in the first to the N-th frames.

At step S304, for each of the pixels, the calculating function 161 calculates an average value of the pixel values in the time direction. For example, the calculating function 161 calculates, for each of the pixels, an average value of the pixel values of the same pixel in the first to the N-th frames.

At step S305, the calculating function 161 calculates, for each of the pixels, a quotient value obtained by dividing the standard deviation by the average value. For example, the calculating function 161 divides the standard deviation of each of the pixels calculated in the process at step S303 by the average value of the pixel calculated in the process at step S304. After that, the calculating function 161 outputs the quotient values resulting from the division as index values.

In other words, the calculating function 161 according to the second embodiment is configured to calculate a fluctuation coefficient in the time direction in each of the multiple positions in the plurality of images, as an index indicating the fluttering in the time direction. As a result, the ultrasound diagnosis apparatus 1 according to the second embodiment is able to calculate the index values each indicating the fluttering in the time direction, without performing the process of eliminating the background component.

OTHER EMBODIMENTS

It is possible to carry out the present disclosure in various different modes other than those described in the embodiments above.

An Image Processing Apparatus

For example, in the embodiments above, the example is explained in which the present disclosure is applied to the ultrasound diagnosis apparatus 1; however, possible embodiments are not limited to this example. For instance, the present disclosure may be applied to an image processing apparatus 200. For example, the image processing apparatus 200 corresponds to a workstation, a Picture Archiving Communication System (PACS) viewer, or the like.

FIG. 11 is a block diagram illustrating an exemplary configuration of the image processing apparatus 200 according to another embodiment. As illustrated in FIG. 11, the image processing apparatus 200 includes an input interface 201, a display 202, storage 210, and processing circuitry 220. The input interface 201, the display 202, the storage 210, and the processing circuitry 220 are connected so as to be able to communicate with one another.

The input interface 201 is an input device such as a mouse, a keyboard, a touch panel, and/or the like configured to receive various types of instructions and setting requests from the operator. The display 202 is a display device configured to display medical images and to display a GUI used by the operator to input the various types of setting requests through the input interface 201.

The storage 210 is structured by using, for example, a Not AND (NAND) flash memory or a Hard Disk Drive (HDD) and is configured to store therein various types of programs used for displaying medical image data and the GUI as well as information used by the programs.

The processing circuitry 220 is an electronic device (a processor) configured to control the overall processes performed by the image processing apparatus 200. The processing circuitry 220 is configured to execute an image processing function 221, a calculating function 222, an index image generating function 223, and an output controlling function 224. For example, the image processing function 221, the calculating function 222, the index image generating function 223, and the output controlling function 224 are recorded in the storage 210 in the form of computer-executable programs. By reading and executing the programs, the processing circuitry 220 realizes the functions (the image processing function 221, the calculating function 222, the index image generating function 223, and the output controlling function 224) corresponding to the read programs.

The image processing function 221 is capable of performing processes that are basically the same as the processes performed by the image processing circuitry 130 illustrated in FIG. 1. Further, the calculating function 222 is capable of performing processes that are basically the same as the processes performed by the calculating function 161 illustrated in FIG. 1. Also, the index image generating function 223 is capable of performing processes that are basically the same as the processes performed by the index image generating function 162 illustrated in FIG. 1.

Similarly, the output controlling function 224 is capable of performing processes that are basically the same as the processes performed by the output controlling function 163 illustrated in FIG. 1.

With these arrangements, for example, in the image processing apparatus 200, the image processing function 221 is configured to perform the speckle noise reducing process on each of a plurality of images that were acquired by using an ultrasound wave and are in a time series. The calculating function 222 is configured to calculate an index value indicating fluttering of image signal intensities in each of multiple positions within a region of interest, on the basis of the plurality of image resulting from the speckle noise reducing process. As a result, the image processing apparatus 200 is able to quantitatively evaluate the fluttering in the images.

Emphasizing the Fluttering by Performing a Filtering Process to Extract a Specific Frequency Component Further, for instance, in the embodiments above, the example is explained in which the temporal fluttering is emphasized by the processes (the LPF process, the speckle noise reducing process, and the difference calculating process) at steps S201 through S203. However, possible processes to emphasize the fluttering are not limited to the processes in this example. For instance, it is also possible to emphasize the temporal fluttering by performing a filtering process to extract a specific frequency component.

In other words, the image processing circuitry 130 may be configured to perform the filtering process to extract only the specific frequency component on the plurality of images. Further, the calculating function 161 is configured to calculate index values on the basis of the plurality of images resulting from the filtering process. In this situation, known examples of the filtering process to extract the specific frequency component include a process performed by an inverse notch filter, which passes only the specific frequency without applying any modification thereto; however, possible embodiments are not limited to this example.

The process to emphasize the fluttering by performing the filtering process to extract the specific frequency component will be explained, with reference to FIGS. 12 and 13. FIGS. 12 and 13 are drawings for explaining the filtering process according to yet another embodiment.

As illustrated in FIG. 12, the image processing circuitry 130 generates a plurality of images I1 by performing a filtering process while using an inverse notch filter on a plurality of images I0. In this situation, the plurality of image I0 subject to the filtering process are, for example, the B-mode images of which the quantity is equal to N and on which the LPF process (step S201) and the speckle noise reducing process (step S202) have been performed. In other words, the image processing circuitry 130 performs the filtering process by using the inverse notch filter on the B-mode images of which the quantity is equal to N and on which the LPF process and the speckle noise reducing process have been performed. As a result, the image processing circuitry 130 generates the images I1 of which the quantity is equal to N and which are obtained by extracting the specific frequency component, from the B-mode images of which the quantity is equal to N and on which the LPF process and the speckle noise reducing process have been performed. After that, the image processing circuitry 130 performs the difference calculating process (step S203) on the images I1 of which the quantity is equal to N resulting from the filtering process, to generate difference images of which the quantity is equal to N−4 (when the frame interval is set to "4").

In this situation, as for the frequency component extracted by the filtering process, it is desirable, for example, to set a frequency component unique to the temporal fluttering. In one example, the image processing circuitry 130 determines the frequency to be extracted by the filtering process, on the basis of a chronological fluctuation in the pixel value (the signal intensity) in a position P1 in the images I0 and a chronological fluctuation in the pixel value in a position P2 in the images I0. In this situation, the position P1 corresponds to a pixel included in a region having the fluttering component. In contrast, the position P2 corresponds to a pixel included in a region having no fluttering component.

FIG. 13 illustrates an example of the filtering process using the inverse notch filter. As illustrated in FIG. 13, the inverse notch filter performs a process of extracting a specific frequency component on the frequency axis. In the top and the bottom sections in FIG. 13, the horizontal axis corresponds to time, whereas the vertical axis corresponds to amplitude. Further, in the middle section of FIG. 13, the horizontal axis corresponds to frequencies, whereas the vertical axis corresponds to normalized amplitude.

As illustrated in the top section of FIG. 13, the pixel values in the position P1 and the pixel values in the position P2 exhibit chronological fluctuations that are different from each other. In this situation, when a Fourier transform is applied to the chronological fluctuation in the pixel value (the amplitude) in each of the positions, the amplitude normalized for each frequency is obtained (the middle section of FIG. 13). In this situation, it is considered that frequencies having a significant difference between the value in the position P1 and the value in the position P2 contain a fluttering component to a large extent. For example, when the value in the position P1 is significantly larger than the value in the position P2 at 0.34 Hz, the image processing circuitry 130 extracts the component at 0.34 Hz. Further, by arranging the frequency components other than the frequency component at 0.34 Hz to be 0, the image processing circuitry 130 obtains the frequency component at 0.34 Hz. After that, by performing an inverse Fourier transform on the frequency component at 0.34 Hz, the image processing circuitry 130 acquires chronological fluctuations of the amplitude obtained by extracting the frequency component at 0.34 Hz with respect to each of the positions P1 and P2 (the bottom section of FIG. 13).

In this manner, the image processing circuitry 130 is configured to obtain the chronological fluctuation in the pixel value in each of the pixel positions, on the basis of the plurality of images I0. Further, the image processing circuitry 130 is configured to perform the Fourier transform on the chronological fluctuation in the pixel value in each of the pixel positions. Further, by performing the inverse Fourier transform while preserving the frequency component at 0.34 Hz, the image processing circuitry 130 is configured to acquire the chronological fluctuation of the amplitude obtained by extracting the frequency component at 0.34 Hz with respect to each of the pixel positions. Further, the image processing circuitry 130 is configured to generate the plurality of image I1 that are arranged in a time series (the right section in FIG. 12) by assigning the amplitude output by the inverse Fourier transform to the pixel positions corresponding to the different times (the temporal phases).

The illustrations in FIGS. 12 and 13 are merely examples, and possible embodiments are not limited to the illustrated examples. For instance, FIG. 12 illustrates the example in which the filtering process to extract the specific frequency component is performed between step S202 and step S203 illustrated in FIG. 4; however, possible embodiments are not limited to this example. For instance, it is possible to perform the filtering process to extract the specific frequency component at any arbitrary time prior to step S205. It should be noted, however, that it is desirable to perform the filtering process to extract the specific frequency component after the radio frequency noise and the speckle noise are reduced (i.e., after step S202), for the purpose of efficiently extracting the fluttering component.

Further, although FIG. 13 illustrates the example in which the frequency component at 0.34 Hz is extracted, possible embodiments are not limited to this example. It is possible to extract a frequency component having an arbitrary value. In other words, the image processing circuitry 130 is able to extract a frequency component having an arbitrary value that is set in advance. Further, as for the value of the frequency extracted by the filtering process, an arbitrary value may be input for each medical examination (for each parametric image taking process). To input the frequency, for example, the operator may input an arbitrary value, or alternatively, a frequency value may be selected from among frequency values that are set at different levels in advance.

Emphasizing the Fluttering by Performing a Converting Process Based on an Orthogonal Coordinate Transformation Further, it is also possible to emphasize the temporal fluttering of a hemangioma, not only by performing the filtering process to extract the specific frequency component, but by performing an orthogonal coordinate transformation.

Figure 14A:
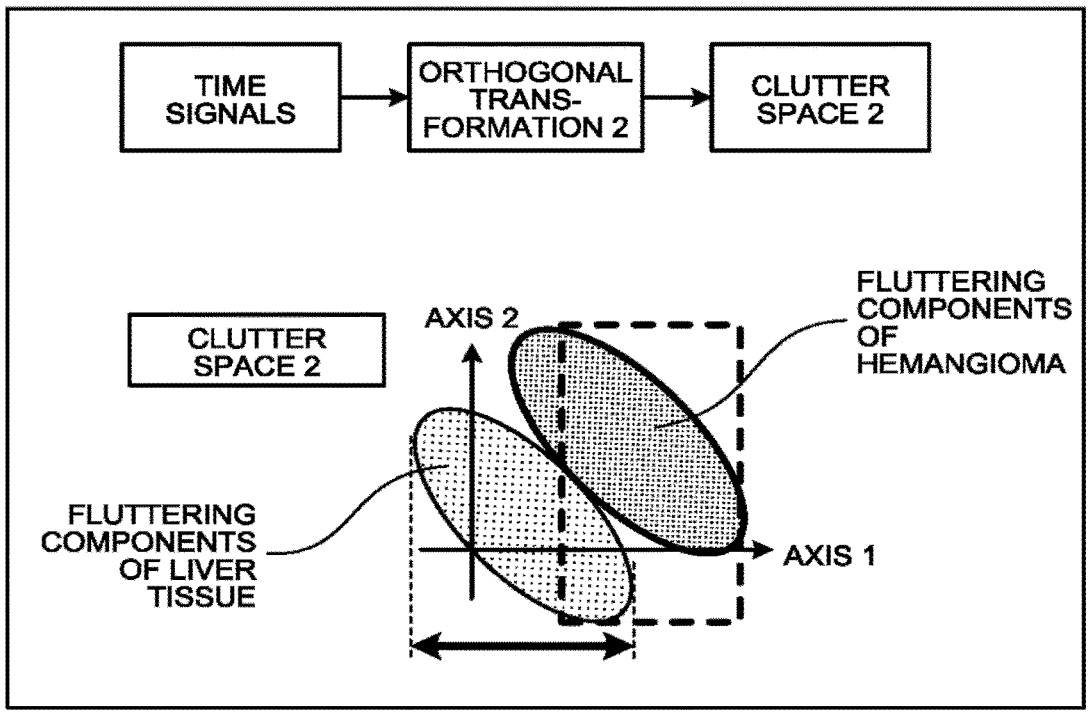
FIGS. 14A and 14B are conceptual diagrams illustrating an orthogonal coordinate transformation.
Figure 14B:
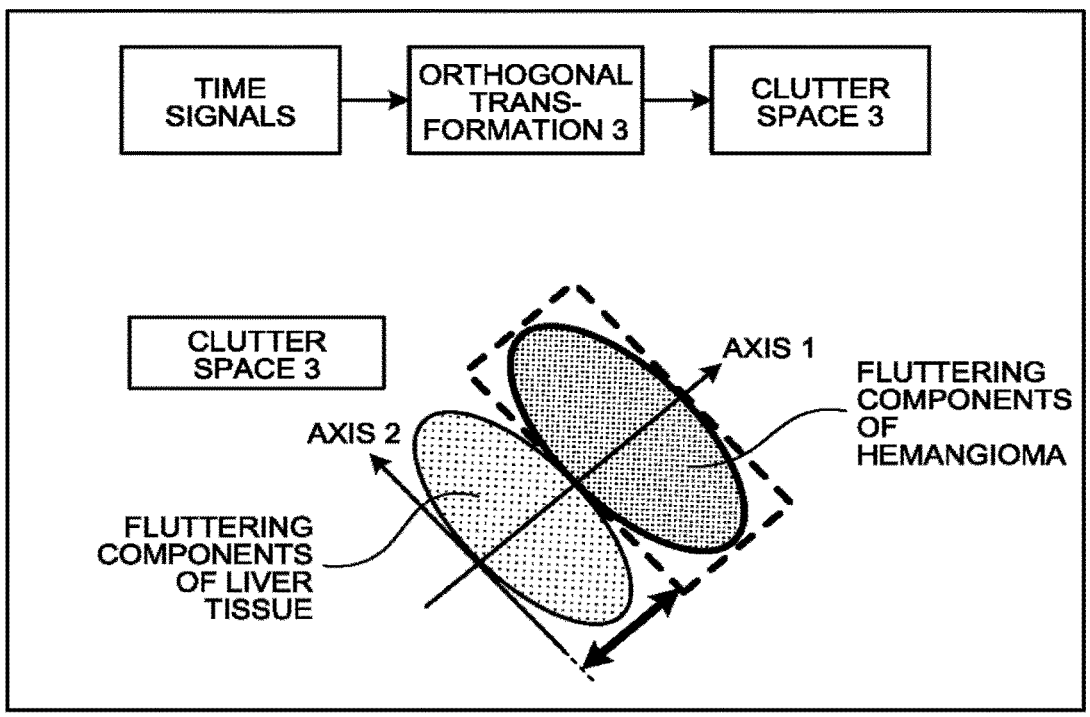
Figure 15:
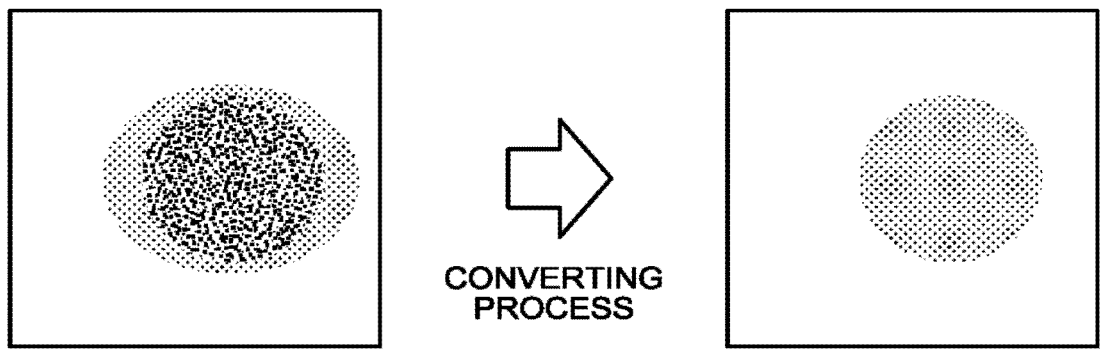
FIG. 15 is a drawing for explaining a converting process according to yet another embodiment.

In other words, the image processing circuitry 130 is configured to generate the plurality of images resulting from the converting process by performing, on the plurality of images, the converting process using the orthogonal coordinate transformation. In other words, the plurality of images resulting from the converting process are obtained by assigning the signal obtained from the orthogonal coordinate transformation to each of the pixel positions. FIGS. 14A and 14B are conceptual diagrams illustrating the orthogonal coordinate transformation. Here, time signals for the fluttering components derived from the background (liver tissue) and the hemangioma are converted into a clutter space by performing the orthogonal coordinate transformation. FIGS. 14A and 14B illustrate an optimum coordinate transformation which allows a clutter space 3 to separate the fluttering components between the hemangioma and the background. FIG. 15 is a drawing for explaining the converting process according to the other embodiment.

More specifically, the image processing circuitry 130 performs the converting process using the orthogonal coordinate transformation, on the B-mode images of which the quantity is equal to N and on which the LPF process and the speckle noise reducing process have been performed. As a result, the image processing circuitry 130 generates the images of which the quantity is equal to N and in which the components having higher ratio of contribution to the principal component analysis are preserved, from the B-mode images of which the quantity is equal to N and on which the LPF process and the speckle noise reducing process have been performed. After that, the image processing circuitry 130 performs the difference calculating process (step S203) on the N images resulting from the converting process to generate difference images of which the quantity is equal to N−4 (when the frame interval is "4").

The situation explained above is merely an example, and possible embodiments are not limited to this example. For instance, in the description above, the example is explained in which the converting process using the orthogonal coordinate transformation is performed between step S202 and step S203 illustrated in FIG. 4; however, possible embodiments are not limited to this example. For instance, it is possible to perform the converting process using the orthogonal coordinate transformation at any arbitrary time prior to step S205. It should be noted, however, that it is desirable to perform the converting process using the orthogonal coordinate transformation after the radio frequency noise and the speckle noise are reduced (i.e., after step S202), for the purpose of efficiently extracting the fluttering component.

An Application to Three-Dimensional Images

Further, for example, although the examples of the processes using the two-dimensional images are explained in the embodiments above, possible embodiments are not limited to those examples. For instance, the present disclosure is applicable to situations where three-dimensional images (volume data) are used.

In other words, the image processing circuitry 130 may be configured to perform a speckle noise reducing process on each of a plurality of three-dimensional images that were acquired by using an ultrasound wave and are in a time series. The calculating function 161 may be configured to calculate an index value indicating fluttering of image signal intensities in each of multiple positions within the region of interest, on the basis of the plurality of three-dimensional images resulting from the speckle noise reducing process. In that situation, it is desirable to configure the output controlling function 163 to generate and display two-dimensional images by performing either a Multi Planar Reconstruction (MPR) process or a volume rendering process on the three-dimensional images.

Displaying a Moving Image

Further, for instance, in the embodiments above, the example is explained in which the single parametric image is displayed from the B-mode images of which the quantity is equal to N and which are arranged in the time series; however, possible embodiments are not limited to this example. For instance, the ultrasound diagnosis apparatus 1 is also capable of displaying the parametric image as a moving image.

In that situation, the ultrasound diagnosis apparatus 1 displays a parametric image in the N-th frame by using the B-mode images in the first to the N-th frames. Subsequently, the ultrasound diagnosis apparatus 1 displays a parametric image in the (N+1)-th frame by using the B-mode images in the second to the (N+1)-th frames. Subsequently, the ultrasound diagnosis apparatus 1 displays a parametric image in the (N+2)-th frame by using the B-mode images in the third to the (N+2)-th frame. In this manner, the ultrasound diagnosis apparatus 1 is able to display the parametric image as a moving image, by updating the plurality of images serving as the processing target, one by one (frame by frame).

The term "processor (circuit)" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). Each of the processors realizes the functions thereof by reading and executing a corresponding program saved in the storage 150. In this situation, instead of saving the programs in the storage 150, it is also acceptable to directly incorporate the programs in the circuits of the processors. In that situation, the processors realize the functions thereof by reading and executing the programs incorporated in the circuits thereof. Further, the processors in the present embodiments do not each necessarily have to be structured as a single circuit. It is also acceptable to structure one processor by combining together a plurality of independent circuits so as to realize the functions thereof. Further, it is also acceptable to incorporate two or more of the constituent elements illustrated in any of the drawings into one processor, to realize the functions thereof.

Further, the constituent elements of the apparatuses illustrated in the drawings are based on functional concepts. Thus, it is not necessary to physically configure the constituent elements as indicated in the drawings. In other words, the specific modes of distribution and integration of the apparatuses are not limited to those illustrated in the drawings. It is acceptable to functionally or physically distribute or integrate all or a part of the apparatuses in any arbitrary units, depending on various loads and the status of use. For example, the functions of the image processing circuitry 130 may be incorporated into the processing circuitry 160. Further, all or an arbitrary part of the processing functions performed by the apparatuses may be realized by a CPU and a computer program analyzed and executed by the CPU or may be realized as hardware using wired logic.

With regard to the processes explained in the embodiments above, it is acceptable to manually perform all or a part of the processes described as being performed automatically. Conversely, by using a method that is publicly known, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

Further, it is possible to realize the image processing methods described in the embodiments above by causing an image processing computer program (hereinafter, "image processing program") prepared in advance to be executed by a computer such as a personal computer, a workstation, or the like. The image processing program may be distributed via a network such as the Internet. Further, the image processing program may be recorded onto a computer-readable recording medium such as a hard disk, a flexible disk (FD), a Compact Disk Read-Only Memory (CD-ROM), a magnetic-optical (MO) disk, a Digital Versatile Disk (DVD), or the like, so as to be executed as being read from the recording medium by a computer.

According to at least one aspect to the embodiments described above, it is possible to quantitatively evaluate the fluttering in the images.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus comprising processing circuitry configured:
   to perform a speckle noise reducing process on each of a plurality of images that were acquired by using ultrasound waves and are in a time series, the plurality of images being a plurality of ultrasound images taken without administration of a contrast agent; and
   to calculate an index value indicating fluttering of image signal intensities caused by a hemangioma in each of multiple positions within a region of interest on each of the plurality of ultrasound images taken without administration of the contrast agent, on a basis of a plurality of images resulting from the speckle noise reducing process.

2. The image processing apparatus according to claim 1, wherein the processing circuitry is further configured to generate a parametric image on a basis of the index values with respect to the multiple positions within the region of interest.

3. The image processing apparatus according to claim 1, wherein, on a basis of the index values in multiple positions within a measured region corresponding to at least a part of the region of interest, the processing circuitry calculates a representative value for the measured region.

4. The image processing apparatus according to claim 1, wherein, before performing the speckle noise reducing process, the processing circuitry performs a low pass filter process in a time direction on the plurality of images.

5. The image processing apparatus according to claim 1, wherein, before performing the speckle noise reducing process, the processing circuitry performs a movement correcting process to correct a movement between images, on the plurality of images.

6. The image processing apparatus according to claim 1, wherein
   the processing circuitry performs a filtering process to extract only a specific frequency component on the plurality of images, and
   the processing circuitry calculates the index values on a basis of a plurality of images resulting from the filtering process.

7. The image processing apparatus according to claim 1, wherein
   the processing circuitry performs, on the plurality oft images, a converting process to extract fluttering of a hemangioma in an orthogonal coordinate transformation, and
   the processing circuitry calculates the index values on a basis of a plurality of images resulting from the converting process.

8. The image processing apparatus according to claim 1, wherein the processing circuitry calculates the index values, after selectively eliminating, from the image signal intensities, a fluttering component of the fluttering.

9. The image processing apparatus according to claim 8, wherein
   the processing circuitry generates a plurality of subtraction images, by performing a subtraction process between the plurality of images resulting from the speckle noise reducing process while using a frame interval set in advance for the plurality of images resulting from the speckle noise reducing process, the subtraction process subtracting pixel intensity values of respective pixels occurring at the frame interval set in advance, and
   the processing circuitry calculates the index values by using the plurality of subtraction images.

10. The image processing apparatus according to claim 9, wherein the processing circuitry performs the subtraction process by using the frame interval designated by an operator.

11. The image processing apparatus according to claim 9, wherein
    the processing circuitry determines the frame interval in accordance with a frequency of fluttering of image signal intensities included in a region that is within the region of interest and is different from a measured region, and
    the processing circuitry performs the subtraction process by using the determined frame interval.

12. The image processing apparatus according to claim 9, wherein
    with respect to each of the plurality of subtraction images, the processing circuitry calculates a summation value by adding together an absolute value of a pixel value of each of the pixels of the respective subtraction image and absolute values of pixel values of surrounding pixels thereof,
    with respect to each of the plurality of images resulting from the speckle noise reducing process, the processing circuitry calculates an average value of the pixel value of each of the pixels of the respective image resulting from the speckle noise reducing process and the pixel values of the surrounding pixels thereof, and
    the processing circuitry calculates each of the index values by using a quotient value obtained by dividing the summation value by the average value.

13. The image processing apparatus according to claim 10, wherein, as the index value, the processing circuitry calculates one selected from between a sum and a statistical value of the quotient values of each of the pixels in the plurality of images resulting from the speckle noise reducing process.

14. The image processing apparatus according to claim 1, wherein, as the index value, the processing circuitry calculates a fluctuation coefficient in a time direction in each of the multiple positions in the plurality of images resulting from the speckle noise reducing process.

15. The image processing apparatus according to claim 1, wherein
the plurality of images are a plurality of B-mode images.

16. An ultrasound diagnosis apparatus comprising;
an image memory configured to store a time series of a plurality of ultrasound images taken by using ultrasound waves without administration of a contrast agent and
a processing circuitry configured:
to perform a speckle noise reducing process on each of the plurality of ultrasound images taken by using ultrasound waves without administration of the contrast agent; and
to calculate an index value indicating fluttering of image signal intensities caused by a hemangioma in each of multiple positions within a region of interest on each of the plurality of ultrasound images taken by using ultrasound waves without administration of the contrast agent, on a basis of a plurality of images resulting from the speckle noise reducing process.

* * * * *